United States Patent [19]

Williams et al.

[11] Patent Number: 5,001,113

[45] Date of Patent: Mar. 19, 1991

[54] DI- OR TRIPEPTIDE RENIN INHIBITORS CONTAINING LACTAM CONFORMATIONAL RESTRICTION IN ACHPA

[75] Inventors: Peter D. Williams, Lansdale; Daniel E. Veber, Ambler, both of Pa.

[73] Assignee: Merck & Co., Inc., Rahway, N.J.

[21] Appl. No.: 492,237

[22] Filed: Mar. 7, 1990

Related U.S. Application Data

[63] Continuation of Ser. No. 403,986, Sep. 6, 1989, abandoned, which is a continuation of Ser. No. 298,815, Jan. 18, 1989, abandoned, which is a continuation of Ser. No. 108,344, Oct. 14, 1987, abandoned.

[51] Int. Cl.$^5$ ............... A61K 37/43; C07K 5/08; C07D 279/10; C07D 265/30
[52] U.S. Cl. .................................. 514/18; 514/19; 530/331; 540/531; 544/58.2; 544/168; 546/216; 546/243
[58] Field of Search ............. 514/18, 19; 530/331; 540/531; 544/58.2, 168; 546/216, 243

[56] References Cited

U.S. PATENT DOCUMENTS 4,705,846 11/1987 Thaisrivongs .................. 530/328

Primary Examiner—Lester L. Lee
Attorney, Agent, or Firm—Mark R. Daniel; Charles M. Caruso

[57] ABSTRACT

Enzyme di- or tripeptides of the formula:

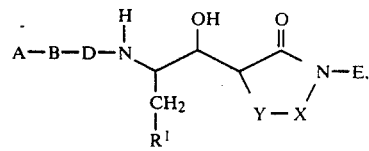

and analogs thereof which inhibit renin and are useful for treating various forms of renin-associated hypertension, hyperaldosteronism and congestive heart failure; compositions containing these renin-inhibitory peptides, optionally with other antihypertensive agents; and methods of treating hypertension, hyperaldosteronism or congestive heart failure or of establishing renin as a causative factor in these problems which employ these novel peptides.

9 Claims, No Drawings

DI- OR TRIPEPTIDE RENIN INHIBITORS CONTAINING LACTAM CONFORMATIONAL RESTRICTION IN ACHPA

This is a continuation, of application Ser. No. 403,986, filed Sept. 6, 1989 now abandoned which is a continuation of U.S.S.N. 298,815 filed Jan. 18, 1989, now abandoned which was a continuation of U.S.S.N 108,344 filed Oct. 14, 1987, and now abandoned.

The present invention is concerned with novel di or tripeptides which inhibit the angiotensinogen cleaving action of the proteolytic enzyme, renin, with pharmaceutical compositions containing the novel peptides of the present invention as active ingredients, with methods of treating renin-associated hypertension, hyperaldosteronism, and congestive heart failure, with diagnostic methods which utilize the novel peptides of the present invention, and with methods of preparing the novel peptides of the present invention.

BACKGROUND OF THE INVENTION

Renin is an endopeptidase (molecular weight about 40,000) produced and secreted by the juxtaglomerular cells of the kidney. Renin has a high specificity for and cleaves the naturally-occurring plasma glycoprotein, angiotensinogen, at only the 10, 11 peptide bond, i.e., between the 10th (Leu) and 11th (Leu) amino acid residues in the equine substrate, as described by Skeggs et al, *J. Exper. Med.* 1957, 106, 439, or between Leu 10 and Val 11 in the human renin substrate, as elucidated by Tewksbury et al., *Circulation* 59, 60, Supp. II: 132, Oct. 1979.

This cleavage of its tetradecapeptide substrate, angiotensinogen, by renin splits off the decapeptide, angiotensin I, which is thought to be hemodynamically-inactive, but which is converted in the lungs, kidney or other tissue by angiotensinconverting enzyme (ACE) to the potent pressor octapeptide, angiotensin II. Angiotensin II then causes constriction of the arterioles and is also believed to stimulate release of the sodium-retaining hormone, aldosterone, from the adrenal gland, thereby causing a rise in extra cellular fluid volume. Thus, the renin-angiotensin system plays an important role in normal cardiovascular homeostasis and in some forms of elevated blood pressure (hypertension).

Inhibitors of angiotensin I converting enzyme have proven useful in the modulation of the renin angiotensin system. Consequently, specific inhibitors of the catalytic and rate-limiting enzymatic step that ultimately regulates angiotensin II production, the action of renin on its substrate, have also been sought as effective investigative tools, as well as therapeutic agents in the treatment of hypertension and congestive heart failure.

Renin antibody, pepstatin (another aspartic proteinase, like renin), phospholipids, and substrate analogs, including tetrapeptides and octa- to tridecapeptides, with inhibition constants ($K_i$) in the $10^{-3}$ $10^{-6}$M region, have been studied.

Umezawa et al., in *J. Antibiot. (Tokyo)* 23: 259–262, 1970, reported the isolation of a peptide, pepstatin, from actinomyces that was an inhibitor of aspartyl proteases such as pepsin, cathepsin D, and renin. Gross et al., *Science* 175:656, 1972, reported that pepstatin reduces blood pressure in vivo after the injection of hog renin into nephrectomized rats. However, pepstatin has not found very wide application as an experimental agent because of its limited solubility and its inhibition of a variety of other acid proteases in addition to renin.

Many efforts have been made to prepare a specific renin inhibitor based on pig renin substrate analogy, since such analogy has been shown to correlate well with and predict human renin inhibitor activity. The octapeptide amino acid sequence extending from histidine-6 through tyrosine 13

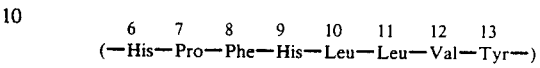

has been shown to have kinetic parameters essentially the same as those of the full tetradecapeptide renin substrate.

Kokubu et al., *Biochem. Pharmacol.*, 22, 3217–3223, 1973, synthesized a number of analogs of the tetrapeptide found between residues 10 to 13, but while inhibition could be shown, inhibitory constants were only of the order of $10^{-3}$M. Analogs of a larger segment of renin substrate have been also synthesized, e.g., Burton et al., *Biochemistry* 14: 892–3898, 1975, and Poulsen et al., *Biochemistry* 12: 3882, 1973, but a lack of solubility and weak binding (large inhibitory constant) generally resulted.

Modifications to increase solubility soon established that the inhibitory properties of the peptides are markedly dependent on the hydrophobicity of various amino acid residues. These modifications also established that increasing solubility by replacing lipophilic amino acids with hydrophilic isosteric residues can become counterproductive. Other approaches to increasing solubility have also had limited success.

Modifications designed to increase binding to renin have also been made, but here too, with mixed results.

A series of inhibitors of renin have been disclosed which contain the unnatural amino acid, statine: see, e.g., Veber et al, U.S. Pat. Nos. 4,384,994 and 4,478,826; Evans et al, U.S. Pat. No. 4,397,786; Boger et al, *Nature*, 1983, 303, 81–84 and U.S. Pat. Nos. 4,470,971; 4,485,099; 4,663,310 and 4,668,770; Matsueda et al, EP-A 128 762, 152 255; Morisawa et al., EP-A 186 977; Riniker et al, EP-A 111 266; Bindra et al, EP-A 155 809; Stein et al, Fed. Proc. 1986, 45, 869; and Holzemann et al, German Offenlegungsschrift DE 3438545. Attempting to explain the effect of statine, Powers et al., in *Acid Proteases, Structure, Function and Biology*, Plenum Press, 1977, 141–157, observed that in pepstatin, statine occupies the space of the two amino acids on either side of the cleavage site of a pepsin substrate and Tang et al., in *Trends in Biochem. Sci.*, 1:205–208 (1976) and *J. Biol. Chem.*, 251:7088–94, 1976, pointed out that the statine residue of pepstatin resembles the transition state for pepsin hydrolysis of peptide bonds.

Renin inhibitors containing other peptide bond isosteres, including a reduced carbonyl isostere have been disclosed by M. Szelke et al, in work described in published European Patent Applications 45 665 and 104 041; in U.S. Pat. No. 4,424,207, and in PCT Int. Appl. WO 84/03044; in *Nature*, 299, 555 (1982); Hypertension, 4, Supp. 2, 59, 1981; and British Patent 1,587,809. In *Peptides, Structure and Function: Proceedings of the Eighth American Peptide Symposium*, ed. V. J. Hruby and D. H. Rich, p. 579, Pierce Chemical Co., Rockford, IL., 1983, Szelke et al also showed isosteric substitutions at the Leu-Leu site of cleavage, resulting in compounds with excellent potency.

Other peptide bond isosteres have then been disclosed in Buhlmayer et al in EP-A 144 290 and 184 550; Hester et al, EP-A 173 481; Raddatz, EP-A 161 588; Dann et al, *Biochem. Biophys Res. Commun.* 1986, 134, 71–77; Fuhrer et al, EP-A 143 746; Kamijo et al, EP-A 181 110; Thaisrivongs et al, *J. Med. Chem.*, 1985, 28, 1553–1555; Ryono et al., EP A 181 071; and Evans et al, U.S. Pat. No. 4,609,641.

Other modifications which have been tried include preparing renin inhibitors with non peptide C-termini, such as disclosed in European Published Applications 172 346 and 172 347; Evans et al, *J. Med. Chem.*, 1985, 28, 1755–1756; Bock et al, *Peptides, Structure and Function: Proceedings of the Ninth American Peptide Symposium*, ed. C. M. Deber et al, pp.751–754, Pierce Chemical Co., Rockford, IL, 1985; and Plattner et al, in *Abstracts from the 191st National Meeting of the Anerican Chemical Society*, April, 1986. Kokubu et al, in *Hypertension*, 1985, 7, Suppl. I, p. 8–10 and Matsueda et al, in *Chemistry Letters*, 1985, 1041–1044 and in European Published Applications 128 762 and 152 255 disclosed peptide aldehyde renin inhibitors, and Hanson et al in *Biochem. Biophys. Res. Commun.* 1985, 132, 155–161, reported peptide glycol inhibitors.

These various renin inhibitors all generally comprise peptide-based inhibitors in which a sequence of the type: ...A—B—D—E—F—G—J—K—L..., where G is a peptide bond mimic and A,B,D,E,F,J,K, and L may individually be absent or may represent naturally-occurring or modified amino acids. Typical sequences of this type include:

```
         7    8    9    10   11   12
... BOC—Pro—Phe—His—Sta—Leu—Phe..., or 8    9    10   11
... BOC—Phe—His—Sta—Leu...,
``` where the N-terminus typically comprises an amino acid protecting group such as BOC or CBZ, and the N-terminal amino acids are Pro—Phe—His or Phe—His.

Lower molecular weight renin-inhibitory di-or tripeptides comprising acyclic 2-substituted-4-amino-5 cycl-ohexyl-3 hydroxy-pentanoic acid (ACHPA) have been disclosed in U.S. Pat. application 45,941, filed May 4, 1987, and other lower molecular weight peptides have been disclosed in Sham, EP 184 855, Bindra et al, EP 155 809, and Matsueda et al, EP 152 255.

It was an object of this invention to prepare lower molecular weight peptides which have enhanced biological potency in inhibiting the renin enzyme. It was also an object to prepare shortened peptide sequences which incorporate at the C terminus a stabilizing, conformationally constrained dipeptide mimic to replace the 10- and 11-position amino acids in the analogous natural substrate. It was a further object to include strategically-located substituents at the C- and/or N-terminii of a shortened peptide which confer increased potency while constructively altering the physical properties of these peptides. It was an additional object of this invention to prepare peptides which have greater oral bioavailability and increased duration of action. It was still a further object of this invention to prepare novel peptides which are more useful antihypertensive agents, and compounds useful in treating hyperaldosteronism and congestive heart failure.

DETAILED DESCRIPTION OF THE INVENTION

The present invention is directed to renin-inhibitory di and tripeptides of the structure:

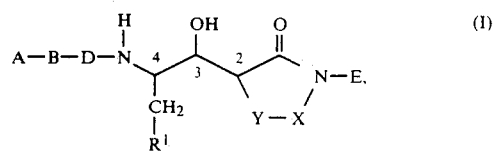

wherein:

A is hydrogen; $C_1$–$C_6$ -alkyl; aryl, where aryl is unsubstituted or mono-, di or trisubstituted phenyl, wherein the substituent(s) is/are independently selected from the group consisting of $C_1$–$C_7$-alkyl, amino, mono- or di-$C_1$–$C_4$-alkylamino, amino-$C_1$–$C_4$-alkyl, hydroxy-$C_1$–$C_4$-alkyl, phenyl-$C_1$–$C_4$-alkyl, mono- or di-$C_1$–$C_4$aklylamino-$C_1$–$C_4$-alkyl, guanidyl, guanidyl$C_1$–$C_4$- alkyl, hydroxyl, $C_1$–$C_4$-alkoxy, trifluoromethyl, halo, CHO, —$CO_2$H, —$CONH_2$, —CONH-$C_1$–$C_4$-alkyl, —CON($C_1$–$C_4$-alkyl)$_2$, —CO-$C_1$–$C_4$-alkyl, —($CH_2$)hd m-13 +N($R^3$)$_2$$R^4$A$^\ominus$, where $R^3$ is $C_1$–$C_4$ alkyl, —($CH_2$)$_4$-, —($CH_2$)$_5$—or —($CH_2$)$_2$-O-($CH_2$)$_2$—; $R^4$ is $C_1$–$C_4$-alkyl, $C_1$–$C_4$-hydroxyalkyl, $C_1$–$C_4$-carboxyalkyl, or —$CH_2$-phenyl; A$^\ominus$ is a counterion selected from the group consisting of single negatively-charged ions, such as chloride, bromide, perchlorate, benzoate, benzene sulfonate, tartrate, maleate, hemitartrate, and acetate; and m is 0-to-3; —$CO_2$-$C_1$–$C_4$-alkyl, —$CO_2$-$C_1$–$C_4$-alkoxy-$C_2$-$C_4$—alkyl,

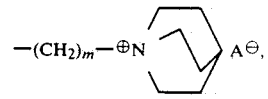

where A$^\ominus$ and m are as defined above, and —$NR^5R^6$, where $R^5$ and $R^6$ are independently hydrogen, unsubstituted or monosubstituted $C_1$–$C_4$-alkyl, wherein the substituent is amino, mono- or di—$C_1$–$C_4$—alkylamino or $\oplus$N($R^3$)$_2$$R^4$ A$^\ominus$, where $R^3$, $R^4$ and are as defined above; Het, where Het is an unsubstituted or mono-or disubstituted 5- or 6-membered mono or bicyclic or benzofused 5 or 6 membered heterocyclic ring, where the one or two heteroatoms are independently selected from the group consisting of N, O, S, NO, SO, $SO_2$ or quaternized N, and the substituent(s) is/are independently selected from the group consisting of hydroxyl, thiol, $C_1$–$C_6$-alkyl, $CF_3$, $C_1$–$C_4$-alkoxy, halo, aryl, as defined above, aryl-$C_1$–$C_4$-alkyl, amino mono- or di $C_1$–$C_4$-alkylamino, amino-$C_1$–$C_4$-alkyl, hydroxy-$C_1$–$C_4$-alkyl, mono or di-$C_1$–$C_4$-alkylamino-$C_1$–$C_4$ -alkyl, guanidyl, guanidyl$C_1$–$C_4$-alkyl, CHO, $CO_2$H, $CO_2$-$C_1$–$C_3$-alkyl, $CONH_2$, CONH-$C_1$–$C_4$-alkyl, CON($C_1$–$C_4$-alkyl)$_2$, $NR^5R^6$,

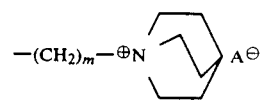

and -($CH_2$)$_m$—$\oplus$N($R^3$)$_2$$R^4$ A$^\ominus$, wherein $R^5$, $R^6$, A$^\ominus$, m, $R^3$ and $R^4$ are as defined above, or when the heteroatom is N, the substituents are alternatively $(CH_2)_q$ or $-(CH_2)_2-O-(CH_2)_2-$ and form a ring with the N-atom, wherein q is 3-to-6;

where $R^2$ is $C_1-C_7$-alkyl; hydrogen; Het, as defined above; aryl, as defined above; mono substituted $C_1-C_5$-alkyl, wherein the substituent is selected from the group consisting of aryl, as defined above; Het, as defined above; hydroxyl; $-CO_2H$; $CO_2R^7$, where $R^7$ is $C_1-C_5$-alkyl, aryl, as defined above, and aryl-$C_1-C_4$-alkyl; $CONH_2$; $-CONH-R^7$ or $-S(O)_n-R^7$, wherein n is 0-to-2 and $R^7$ is as defined above; $C_1-C_4$-alkoxy; $C_3-C_7$-cycloalkyl; amino; mono- or di-$C_1-C_4$-alkylamino; NH-aryl, $-NH-CH_2$-aryl or $-CO$-aryl, where aryl is as defined above; and $-NH$-Het, $-NH-CH_2$-Het or $-CO$-Het, where Het is as defined above;

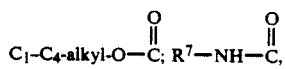

where $R^7$ is as defined above; or

where $R^9$ is $C_1-C_5$-alkyl, aryl, as defined above, or Het, as defined above;

B and D are independently

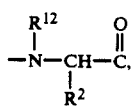

where $R^{12}$ is hydrogen, $C_1-C_5$-alkyl or $CH_2$-aryl, wherein aryl is as defined above; and $R^2$ is as defined above;

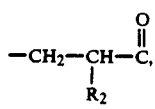

where $R^2$ is as defined above; or either B or D, but not both simultaneously, is absent;

$R^1$ is hydrogen; $C_3-C_6$-alkyl; aryl, as defined above; unsubstituted, mono-, di- or trisubstituted $C_3-C_7$-cycloalkyl, where the substituent(s) is/are selected from the group consisting of $C_1-C_4$-alkyl, trifluoromethyl, hydroxyl, $C_1-C_4$-alkoxy and halo; or unsubstituted or 4-monosubstituted 1,3-dithiolan-2-yl or unsubstituted or 4-mono-substituted 1,3-dithian-2-yl, where the substituent is $(CH_2)_m$ aryl, where m and aryl are as defined above;

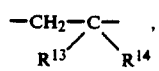

where $R^{13}$ and $R^{14}$ are independently hydrogen; $C_1-C_7$-alkyl; $C_2-C_7$-alkenyl; $-CO_2H$; $-CONH_2$; $CO_2R^7$, $-CO-NH-R^7$ or $-CO-N(R^7)$, wherein $R^7$ is as defined above; mono-substituted $C_1-C_5$-alkyl, wherein the substituent is selected from the group consisting of azido; halo; hydroxy; $C_1-C_5$-alkoxy; aryl, aryl-$CH_2O$, aryloxy, aryl-$COO-$, aryl-$CH_2$ $-NH-$ or arylamino, where aryl is as defined above; $C_1-C_5$-alkyl-$CO_2-$; $R^7NH-COO-$, $R^7-CO-NH-$, $R^7-NH-CO-NH-$ or $R^7-S(O)_n$, where n and $R^7$ are as defined above; amino; mono or di-$C_1-C_4$-alkylamino; and Het, as defined above; or $R^{13}$ and $R^{14}$ are connected to form a polymethylene chain of the formula, $-(CH_2)_p$, where p is 2 to 6; or

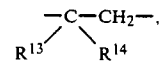

where $R^{13}$ and $R^{14}$ are as defined above;

Y is $CH_2$, O, S, SO or $SO_2$; or

Y—X is $-(CH_2)_4-$; and

E is hydrogen; aryl, as defined above; Het, as defined above; $C_2-C_7$-alkenyl; or unsubstituted or mono-substituted $C_1-C_7$-alkyl or unsubstituted or mono-substituted $C_3-C_7$-cycloalkyl, where the substituent is selected from the group consisting of aryl, $-CO$ aryl, $-NH-$aryl or $-O-$aryl, wherein aryl is as defined above; Het, $-NH-$Het, $-O-$Het, $-CO-$Het, $-NH-CO-$Het, $CO-NH-$Het, $-CO-NH-CH_2-$Het or $-O-CO-$Het, wherein Het is as defined above; azido; $C_3-C_7$-cycloalkyl; halo; hydroxyl; $C_1-C_4$-alkoxy; $-COOH$; $-O-CO-R^7$, $-O-CO-NH R^7$, $-NH-CO-R^7$, $-NH-CO-NH R^7$, $-S(O)_n-R^7$, $-CO_2R^7$ or $-CO-NH-R^7$, wherein $R^7$ and n are as defined above; amino; mono- or di $C_1-C_4$-alkylamino; CHO; and $-\oplus N(R^3)_2R^8 A^\ominus$,

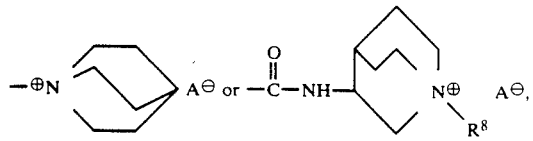

where $R^8$ is $C_1-C_4$-alkyl, $C_1-C_4$hydroxyalkyl, $C_1-C_4$-carboxyalkyl, $-CH_2$-aryl, wherein aryl is as defined above, or $-CH_2-$Het, wherein Het is as defined above, and $R^3$ and $A^\ominus$ are as defined above; and pharmaceutically acceptable salts thereof.

In the peptides of the present invention, the components having asymmetric centers occur as racemates, racemic mixtures and as individual diastereomers, with all isomeric forms generally being included in the present invention. In particular, asymmetric carbon atoms at the 2, 3 and 4 positions in peptides of Formula I preferably have an S configuration.

When any variable (e.g., aryl, Het, m, n, $R^2$, $R^3$, $R^7$, $A^-$, etc.) occurs more than one time in any variable or in formula I, its definition on each ocurrence is independent of its definition at every other occurrence.

As used herein, "alkyl" is intended to include both branched- and straight chain saturated aliphatic hydrocarbon groups having the specified number of carbon atoms (Me is methyl, Et is ethyl); "alkoxy" represents an alkyl group of indicated number of carbon atoms attached through an oxygen bridge; and "$C_3-C_7$-cycloalkyl" is intended to include saturated ring groups, such as cyclopropyl, cyclobutyl, cyclopentyl, cyclohexyl and cycloheptyl. "Alkanoyl" is intended to include those alkylcarbonyl groups of specified number of carbon atoms, which are exemplified by formyl, acetyl, propanoyl and butanoyl; "alkenyl" is intended to include hydrocarbon chains of either a straight or branched- configuration and one unsaturation, which may occur at any point along the chain, such as ethenyl, propenyl, butenyl, pentenyl, and the like, and includes E and Z forms, where applicable; and "arylalkyl" represents aryl groups as herein defined which are attached through a straight- or branched- chain alkyl group of specified number of carbon atoms, such as, for example, benzyl, phenethyl, 3,3-diphenylpropyl, 3-indolymethyl, and the like. "Halo", as used herein, means fluoro, chloro, bromo and iodo, and "counterion" is used to represent a small, single negatively-charged specie, such as chloride, bromide, hydroxide, nitrate, acetate, benzoate, perchlorate, benzene sulfonate, tartrate, hemitartrate, maleate, and the like.

As used herein, with exceptions as noted, "aryl" is intended to mean phenyl (Ph), which is optionally-substituted by from one- to three- members independently selected from the group consisting of $C_1$-$C_7$-alkyl, amino (Am), mono- or di-$C_1$-$C_4$-alkylamino, phenyl $C_1$-$C_4$-alkyl, amino-$C_1$-$C_4$alkyl, hydroxy-$C_1$-$C_4$-alkyl, mono or di-$C_1$-$C_4$-alkylamino-$C_1$-$C_4$-alkyl, hydroxyl, guanidyl, guanidyl-$C_1$-$C_4$-alkyl, $C_1$-$C_4$-alkoxy, $CF_3$, halo, CHO, $CO_2H$, $CONH_2$, CONH—$C_1$-$C_4$-alkyl, CON($C_1$-$C_4$)$_2$, CO—$C_1$-$C_4$-alkyl or $(CH_2)_m$—$^\oplus N(R^3)_2 R^4 A^\ominus$, wherein $R^3$, $R^4$ and m are as defined above and $A^\ominus$ is counterion, as defined herein. "Aroyl" is intended to include those aryl carbonyl groups which are exemplified by phenoyl.

The term "Het", as used herein, represents a 5- to 7-membered mono- or bicyclic heterocyclic ring which is either saturated or unsaturated, and which consists of carbon atoms and one or two heteroatoms selected from the group consisting of N, O and S, and wherein the nitrogen and sulfur heteroatoms may optionally be oxidized, and the nitrogen heteroatom may optionally be quaternized, and including any bicyclic group in which any of the above defined heterocyclic rings is fused to a benzene ring. Heterocycles which contain nitrogen are preferred. In the case of a heterocyclic ring containing one or more nitrogen atoms, the point of attachment may be at one of the nitrogen atoms, or at any carbon atom. Examples of such heterocyclic elements include piperidyl, piperidinyl, piperazinyl, 2-oxopiperazinyl, 2 oxopyrolodinal, 2-oxopiperidinyl, 2-oxoazepinyl, azepinyl, pyrryl, pyrrolinyl, 4-piperidonyl, pyrrolidinyl, pyrazolyl, pyrazolinyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinucli-dinyl, isothiazolidinyl, indolyl, guinolinyl, isoguinolinyl, benzimidazolyl, benzothiazolyl, benzoxazolyl, furyl, thienyl, benzothienyl, thiamorpholinyl, thiamorpholinyl sulfoxide, and thiamorpholinyl sulfone. The heterocyclic moiety is further optionally-substituted by from one to four- members independently selected from the group consisting of hydroxyl, thiol, $C_1$-$C_6$-alkyl, $CF_3$, $C_1$-$C_4$-alkoxy, halo, aryl, aryl-$C_1$-$C_4$-alkyl, amino, mono- or di-$C_1$-$C_4$-alkylamino, amino-$C_1$-$C_4$-alkylamino, amino-$C_1$-$C_4$-alkyl, hydroxy-$C_1$-$C_4$-alkyl, di-$C_1$-$C_4$-alkylamino-$C_1$-$C_4$-alkyl, guanidyl, guanidyl $C_1$-$C_4$-alkyl, CHO, $CO_2H$, $CO_2$-$C_1$-$C_4$-alkyl, $CONH_2$, CONH-$C_1$-$C_4$-alkyl, CON($C_1$-$C_4$-alkyl)$_2$, —$NR^5R^6$,

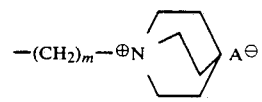

or —$(CH_2)_m$—$^\oplus N(R^3)_2 R^8 A^\ominus$,
wherein $R^5$, $R^6$, $A^\ominus$, m, $R^3$ and $R^8$ are as defined above, or when the heteroatom is N, the substituents on the N-atom are -13 $(CH_2)_q$—or —$(CH_2)_2$—O—$(CH_2)_2$—and form a ring with the N-atom, wherein q is as defined above.

The following additional abbreviations have also been used herein:

| Abbreviated Designation | Amino Acid/Residue |
|---|---|
| ACHPA | (3S,4S)-4-amino-5-cyclohexyl-3-hydroxypentanoic acid |
| Ala | L-alanine |
| Arg | L-arginine |
| Cys | cysteine |
| Gly | L-glycine |
| His | D- or L-histidine |
| HomoPhe | homologated phenylalanine |
| HomoTrp | homologated tryptophan |
| HomoTyr | homologated tyrosine |
| Ile | L-isoleucine |
| Leu | L-leucine |
| Lys | L-lysine |
| Met | L-methionine |
| Nle | norleucine |
| Nva | norvaline |
| Orn | L-ornithine |
| (p-MeO)Phe | L-para-methoxyphenylalanine |
| Phe | L-phenylalanine |
| Pro | proline |
| Sar | L-sarcosine (N-methylglycine) |
| Ser | L-serine |
| Sta | statine |
| Thr | L-threonine |
| Trp | L-tryptophan |
| Tyr | L-tyrosine |
| Val | L-valine |
| Protecting Group | |
| BOC | t-butyloxycarbonyl |
| CBZ | benzyloxycarbonyl(carbobenzoxy) |
| DNP | 2,4-dinitrophenyl |
| IPOC | isopropoxycarbonyl |
| Activating Group | |
| HBT(HOBt) | 1-hydroxybenzotriazole hydrate |
| HOSU | N-hydroxysuccinimide |
| Condensing Agent | |
| DCCI (DCC) | dicyclohexylcarbodiimide |
| DPPA | diphenylphosphorylazide |
| EDC | 1-(3-dimethylaminopropyl)-3-ethyl carbodiimide hydrochloride |
| Reagent | |
| (BOC)$_2$0 | di-t-butyl dicarbonate |
| DIBAL | diisobutylaluminum hydride |
| DIPEA | diisopropylethylamine |
| DMAP | 4-(dimethylamino)pyridine |
| TEA | triethylamine |
| TFA | trifluoroacetic acid |
| LAH | lithium aluminum hydride |
| LDA | lithium diisopropylamide |
| MCPBA | 3-chloroperoxybenzoic acid |
| NMM | N-methyl morpholine |
| PPTS | pyridinium para-toluenesulfonate |
| TBAF | tetra-n-butylammonium fluoride |
| Solvent | |
| HOAc (AcOH) | acetic acid |
| DMF | dimethylformamide |
| DMSO | dimethyl sulfoxide |
| EtOAc | ethyl acetate |

| Abbreviated Designation | Amino Acid/Residue |
|---|---|
| EtOH | ethanol |
| Et₂O | ether |
| MeOH | methanol |
| THF | tetrahydrofuran |

The novel renin inhibitory peptides of the present invention may be generalized and alternately described in terms of common amino acid components and closely-related analogs thereof, in accordance with formula I, wherein A, $R^1$, X and E are as defined under Formula I;

B is Absent, Ala, Leu, Phe, HomoPhe, (p—MeO)-Phe, Tyr, Trp, HomoTrp or

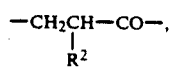

where $R^2$ is as defined above; and

D is Absent, Ala, Ser, Met, Thr, Phe, Tyr, Trp, His, Lys, Orn, Arg or Val, such that B and D are not simultaneously absent.

In terms of substrate analogy, a unique aspect and essential feature of the present invention is the substitution of the

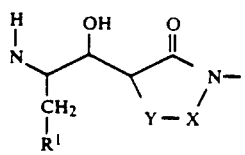

component for the double amino acid sequence, Leu¹⁰-Val¹¹ in the endogenous human renin substrate

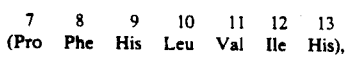

which substitution for both amino acids at the cleavage site rather than just one is believed to result in an improved substrate analogy. This invention's peptides particularly comprise novel lactam versions of rigid 4-amino-5-cyclohexyl-3-hydroxy-pentanoic acid (ACHPA), which enables stereo-specific placement of substituents, and allows the

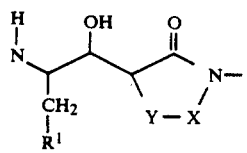

component to better mimic the Leu¹⁰-Val¹¹ dipeptide moiety in the natural substrate.

It will be understood that closely-related analogs of the above common amino acids, for example, aliphatic amino acids in addition to Ala, Val, Leu, and Ile, such as α-aminobutyric acid (Abu), substituted phenyl derivatives of Phe, and Nα-methyl amino acids, are included in the broad description of the novel inhibitory peptides of the present invention represented by Formula I and related definitions.

Preferred renin-inhibitory peptides are those wherein A is $R^2$—CO—, $R^9$—SO₂—, C₁-C₄-alkyl-O-CO—or $R^7$—NH—CO—, wherein $R^2$, $R^7$ and $R^9$ are as defined above; B is absent (when D is present), L-phenylalanyl or derivatives thereof substituted on the aromatic ring by para-methoxy or $$-CH_2-\overset{(S)}{\underset{CH_2Ph}{CH}}-CO-;$$

D is absent (when B is present), L-histidyl or L valinyl; $R^1$ is cyclohexyl; Y is O or CH₂; $R^{13}$ and $R^{14}$ in either definition of X are simultaneously or independently hydrogen or methyl; and E is C₁-C₆-alkyl, —(CH₂)ᵣ—⊕N(R³)₂R⁸ CH₃CO⊖₂, wherein r is 2 or 3 and $R^3$ and $R^8$ are as defined above,

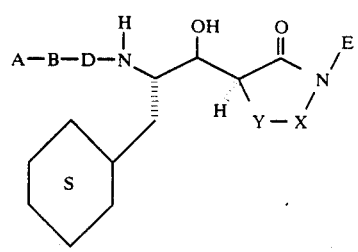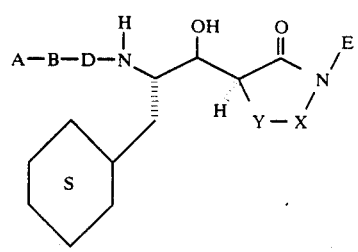

wherein $R^8$ is as defined above. The preferred stereochemistry at the 2,3 and 4 positions is S.

Representative preferred renin-inhibitory peptides of the present invention include the following compounds having the structure:

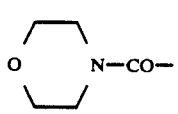

wherein in the structures:

| | A | B | D | Y | X | E |
|---|---|---|---|---|---|---|
| 1 | Boc (CH₃)₂CHSO₂— | Phe " | His " | —CH₂— " | —CH₂CH₂— " | n-Bu " |
| | ![morpholine]O⟨ ⟩N—CO— | " | " | " | " | " |
| | (CH₃)₂CHSO₂— | —CH₂CH(CH₂Ph)—CO— | " | " | " | " |

-continued

| | A | B | D | Y | X | E |
|---|---|---|---|---|---|---|
| 5 | — | indol-2-yl-CO— | " | " | " | " |
| | Boc<br>(CH₃)₂CHSO₂— | Phe<br>" | His<br>" | —CH₂<br>" | —CH₂C(CH₃)₂—<br>" | n-Bu<br>" |
| | morpholino-N—CO— | " | " | " | " | " |
| | (CH₃)₂CHSO₂— | CH₂CH(CH₂Ph)—CO— | " | " | " | " |
| 10 | — | indol-2-yl-CO— | " | " | " | " |
| | Boc | " | " | " | —CH₂CH₂— | —(CH₂)₂—N⊕(Et)₂CH₂Ph<br>OAc⊖ |
| | (CH₃)₂CH—SO₂— | " | " | " | " | " |
| | morpholino-N—CO— | " | " | " | " | " |
| | (CH₃)₂CH—SO₂— | CH₂CH(CH₂Ph)—CO— | His | —CH₂ | —CH₂CH₂— | —(CH₂)₂—N⊕(Et)₂CH₂Ph<br>OAc⊖ |
| 15 | — | indol-2-yl-CO— | " | " | " | " |
| | Boc<br>(CH₃)₂CHSO₂— | Phe<br>" | "<br>" | —O—<br>" | "<br>" | "<br>" |
| | morpholino-N—CO— | " | " | " | " | " |
| | (CH₃)₂CH—SO₂— | CH₂CH(CH₂Ph)—CO— | " | " | " | " |
| 20 | — | indol-2-yl-CO— | " | " | " | " |
| | Boc | Phe | His | —CH₂— | —C(CH₃)₂CH₂— | —(CH₂)₂N⊕(Et)₂CH₂Ph<br>OAc⊖ |
| | (CH₃)₂CHSO₂— | " | " | " | " | " |

-continued

| | A | B | D | Y | X | E |
|---|---|---|---|---|---|---|
| | O(CH₂CH₂)₂N—CO— | " | " | " | " | " |
| | (CH₃)₂CH—SO₂— | CH₂CH(CH₂Ph)—CO— | " | " | " | " |
| 25 | — | indol-2-yl-CO— (2-indolylcarbonyl) | " | " | " | " |
| | Boc | Phe | His | —CH₂— | —CH₂CH₂— | HC(CH₂CH₂)₂N⁺(Et)₂ ⊖OAc |
| | (CH₃)₂CHSO₂— | " | " | " | " | " |
| | O(CH₂CH₂)₂N—CO— | " | " | " | " | " |
| | (CH₃)₂CH—SO₂— | CH₂CH(CH₂Ph)—CO— | " | " | " | " |
| 30 | — | indol-2-yl-CO— | " | " | " | " |
| | Boc | Phe | His | —CH₂— | —CH₂CH₂— | HC(CH₂CH₂)₂N⁺(CH₂Ph) ⊖OAc |
| | (CH₃)₂CHSO₂— | " | " | " | " | " |
| | O(CH₂CH₂)₂N—CO— | " | " | " | " | " |
| | (CH₃)₂CH—SO₂— | CH₂CH(CH₂Ph)—CO— | " | " | " | " |
| 35 | — | indol-2-yl-CO— | " | " | " | " |

The pharmaceutically-acceptable salts of the peptides of Formula I (in th form of water- or oil-soluble or dispersible products) include the conventional non-toxic salts or the quarternary ammonium salts of these peptides which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, c-cylopentan-epropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2 hydroxyethanesulfonate, lactate, maleate, methanesulfonate, 2 naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

Chemical synthesis of the compounds with the general structure given in formula I may be accomplished in several ways as illustrated by the following generalized procedures (wherein "ACHP", an abbreviation of 2-Amino-3-Cyclohexyl 1-HydroxyPropyl, is used in describing the structural segment which joins the A-B-D and

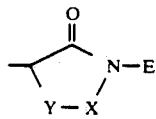

portions of the invention as shown in formula I. The ACHP segment is connected through the 1-position of the propyl chain to the 3-position of the piperidinone or caprolactam, to the 2-position of the morpholinone or thiamorpholinone, and through the amino group to the A-B-D segment.)

Method A:

Step A1. A derivative of 2-piperidinone, caprolactam, 3 morpholinone or 3-thiamorpholinone is obtained through commercial sources or is prepared using well known chemical methods for preparation of members in these classes (see Example 1);

Step A2. The enolate of the 2 piperidinone, caprolactam, 3-morpholinone or 3-thiamorpholinone derivative is generated, such as by using LDA as the base, and is added to a nitrogen-protected (e.g., N—Boc or N—CBZ protected) α-amino-aldehyde (e.g., N-tert butyloxycarbonyl cyclohexylalaninal) to give a Boc- or CBZ-protected amino alcohol derivative (see Example 2B);

Step A3. The nitrogen protecting group of the amino alcohol derivative from step A2 is removed (e.g., by hydrogenolysis for CBZ protection, or TFA treatment for Boc protection) and the amine is coupled using standard peptide methodology to one or two amino acids, or to an appropriate carboxylic acid, the structure(s) of which is/are described by A, B, and D in the general formula I (e.g., see Example 3A steps 1 and 2); and Step A4. Removal of any protecting groups which may have been used, e.g., on the lactam substituent(s) $R^{13}$, $R^{14}$, or E), or on the amino acid side chains (see Example 3A, step 3), gives the final products.

Method B:

Steps A1 and A2 are followed.
Step B3. Modification of the lactam substituent(s) ($R^{13}$, $R^{14}$, and E in generic formula I) is/are performed, as shown in Examples 2V-2PP.

Then Steps A3 and A4 are followed.

Method C:

Steps A1, A2 and A3 are followed.
Step C4: Modification of the lactam substituent(s) $R^{13}$, $R^{14}$, and E in generic formula I) is/are performed, as shown in Examples 3D.
Step A4 is then followed.

The novel peptides of the present invention possess a high degree of activity in treating renin-associated hypertension, hyperald-osteronism and/or congestive heart failure in humans, as well as in other warm-blooded animals such as mice, rats, horses, dogs and cats.

For these purposes, the peptides of the present invention may be administered orally, parenterally (including subcutaneous injections, intravenous, intramuscular, intrasternal injection or infusion techniques), by inhalation spray, or rectally, in dosage unit formulations containing conventional non-toxic, pharmaceutically acceptable carriers, adjuvants and vehicles.

Thus, in accordance with the present invention there is further provided a method of treating and a pharmaceutical composition for treating renin-associated hypertension, hyperaldosteronism, and/or congestive heart failure. This treatment involves administering to a patient in need of such treatment a pharmaceutical composition comprising a -pharmaceutical carrier, optionally with an adjuvant, and a therapeutically-effective amount of a peptide of the formula:

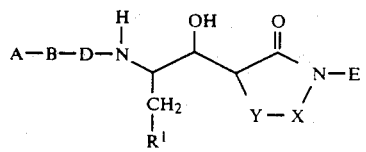

wherein A, B, D, $R^1$, X, Y and E are defined above, or a pharmaceutically-acceptable salt thereof.

These pharmaceutical compositions may be in the form of orally-administrable suspensions or tablets; nasal sprays; sterile injectable preparations, for example, as sterile injectable aqueous or oleagenous suspensions; or suppositories.

When administered orally as a suspension, these compositions may contain microcrystalline cellulose for imparting bulk, alginic acid or sodium alginate as a suspending agent, methylcellulose as a viscosity enhancer, and sweetners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions may be prepared as solutions in saline, employing benzyl alcohol or other suitable preservatives, absorption promoters to enhance bioavailability, flourocarbons, and/or other solubilizinq or dispersing agents known in the art.

The injectable solutions or suspensions may be formulated according to known art, using suitable non-toxic, -parenterally-acceptable diluents or solvents, such as mannitol, 1,3 butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non irritating excipient, such as cocoa butter, synthetic glyceride esters or polyethylene glycols, which are solid at ordinary temperatures, but liquify and/or dissolve in the rectal cavity to release the drug.

Dosage levels of the order of 0.02 to 2.0 grams-per-day are useful in the treatment of the above-indicated conditions, with oral doses two-to five times higher. For example, renin-associated hypertension and hyperaldosteronism are effectively treated by the administration of from 10 to 50 milligrams of the compound per kilogram of body weight from one to three times per day. It will be understood, however, that the specific dose level and frequency of dosage for any particular patient will depend upon a variety of factors including the activity of the specific compound employed, the metabolic stability and length of action of that compound, the age, body weight, general health, sex, diet, mode and time of administration, rate of excretion, drug combination the severity of the particular condition, and the host undergoing therapy.

The present invention is also directed to combinations of the novel renin-inhibitory peptides of Formula I with one or more antihypertensive agents selected from the group consisting of diuretics, α-and/or β-adrenergic blocking agents, CNS-acting agents, adrenergic neuron blocking agents, vasodilators, angiotensin I converting enzyme inhibitors, calcium channel blockers, and other antihypertensive agents.

For example, the compounds of this invention can be given in combination with such compounds or salt or other derivative forms thereof as:

Diuretics: acetazolamide; amiloride; bendro flumethiazide; benzthiazide; bumetanide; chlorothiazide; chlorthalidone; cyclothiazide; ethacrynic acid; furosemide; hydrochlorothiazide; hydro flumethiazide; indacrinone (racemic mixture, or as either the (+) or (−) enantiomer alone, or a manipulated ratio, e.g., 9:1 of said enantiomers, respectively); metolazone; methyclothiazide; muzolimine; polythiazide; guinethazone; sodium ethacrynate; sodium nitroprusside; spironolactone; ticrynafen; triamterene; trichlormethiazide; α-Adrenergic Blocking Agents: dibenamine; phentolamine; -phenoxybenzamine; prazosin; tolazoline; β-Adrenergic Blocking Agents: atenolol; metoprolol; nadolol; propranolol; timolol;

((+)-2-[3-(tert-butylamino) 2-hydroxypropoxy]-2-furananilide) (ancarolol);
(2 acetyl-7-(2-hydroxy-3-isopropy-lamincpropoxy)-benzofuran HCl) (befunolol);
((±; 1-(isopropylamino) 3-(p-(2-cyclopropylmethoxyethyl)-phenoxy)-2-propranol HCl) (betaxolol);
(1-[(3,4-dimethoxyphenethyl)amino]-3-(m-tolyloxy)-2-propanol HCl) (bevantolol);
((±)-1-(4-((2-isopropoxyethoxy)methyl)phenoxy)-3-isopropylamino-2-propanol)fumarate) (bisoprolol);
(4-(2-hydroxy-3-[4-(phenoxymethyl)-piperidino]-propoxy)-indole);
(carbazolyl-4-oxy-5,2-(2-methoxyphenoxy)-ethylamino-2-propanol);
(1-((1,1-dimethylethyl)amino)-3-((2-methyl-1H-indol-4-yl)oxy)-2-propanol benzoate) (bopindolol);
(1-(2-exobicyclo[2.2.1]-hept-2-ylphenoxy)3-[(1-methylethyl)amino]-2-propanol HCl) (bornaprolol);
(o [2-hydroxy-3-[(2-indol-3-yl-1,1-dimethylethyl)amino]propoxy]benzonitrile HCl) (bucindolol);
(α[(tert.butylamino)methyl]-7-ethyl-2-benzofuranmethanol) (bufuralol);
(3-[3-acetyl-4-[3-(tert.butylamino)-2-hydroxypropyl]-phenyl]1,1-diethylurea HCl) (celiprolol);
((±)-2-[2-[3-[(1,1-dimethylethyl)amino]-2-hydroxypropoxy]phenoxy]-N-methylacetamide HCl) (cetamolol);
(2-benzimidazolyl-phenyl(2-isopropylamino-propanol));
((±) 3'-acetyl-4'-(2-hydroxy-3-isopropylamino-propoxy)acetanilide HCl) (diacetolol);
(methyl-4-[2-hydroxy3-[(1-methylethyl)amino-propoxy]]-benzenepropanoate HCl) (esmolol);
(erythro DL-1-(7-methylindan4-yloxy)-3-isopropylaminobutan 2 ol);
(1-(tert.butylamino)-3-[O-(2-propynyloxy)phenoxy]-2-propanol (pargolol);
(1-(tert.butylamino)-3-[o-(6-hydrazino-3-pyridazinyl)-phenoxy]-2-propanol diHCl) (prizidilol);
((−)-2-hydroxy-5-[(R)-1-hydroxy-2-[(R)-(1-methyl-3-phenylpropyl)amino]ethyl]benzamide);
(4-hydroxy-9-[2-hydroxy-3-(isopropylamino)-propoxy]-7-methyl-5H-furo[3,2-g][1]benzopyran-5-one) (iprocrolol);
((−)-5-(tert.butylaaino)-2-hydroxypropoxy]-3,4-dihydro1-(2H)-naphthalenone HCl) (levobunolol);
(4-(2-hydroxy-3-isopropylamino-propoxy)-1,2-benzisothiazole HCl);
(4-[3-(tert.butylamino)-2-hydroxypropoxy]-N-methylisocarbostyril HCl);
((±)-N-2-[4-(2-hydroxy-3-isopropyl aminopropoxy)-phenyl]ethyl N'-isopropylurea) (pafenolol);
(3-[[(2-trifluoroacetamido)ethyl]amino]-1-phenoxy-propan-2-ol);
(N-(3-(o -chlorophenoxy)-2-hydroxypropyl)-N'-(4'-chloro2,3 -dihydro-3-oxo-5-pyridazinyl) ethylenediamine);
((±) N-[3-acetyl-4-[2-hydroxy-3-[(1-methylethyl)amino]-propoxy]phenyl]butanamide) (acebutolol);
((±)-4'-[3-(tert-butylamino)-2-hydroxypropoxy]-spiro[cyclohexane 1,2'-indan]-1'-one) (spirendolol);
(7-[3-[[2-hydroxy-3-[(2-methylindol-4-yl)oxy]propyl]amino]butyl]thiophylline) (teoprolol);
((±) 1-tert.butylamino-3-(thiochroman-8-yloxy)-2-propanol) (tertatolol);
((±)-1-tert.butylamino-3-(2,3-xylyloxy)-2-propanol HCl) (xibenolol);
(8-[3-(tert.butylamino)-2-hydroxypropoxy]-5-methylcoumarin) (bucumolol);
(2-(3-(tert.butylamino)-2-hydroxy-propoxy)benzonitrile HCl) (bunitrolol);
((±)-2'-[3-(tert-butylamino)-2-hydroxypropoxy-5'-fluorobutyrophenone) (butofilolol);
(1-(carbazol-4-yloxy)-3-(isopropylamino)-2-propanol) (carazolol);
(5-(3-tert.butylamino-2-hydroxy)propoxy-3,4-dihydrocarbostyril HCl) (carteolol);
(1 (tert.butylamino)-3-(2,5-dichlorophenoxy)-2-propanol) (cloranolol);
(1-(inden-4(or 7)-yloxy)-3-(isopropylamino)-2-propanol HCl) (indenolol);

(1-isopropylamino-3-[(2-methylindol-4-yl)oxy]-2-propanol) (mepindolol);

(1-(4-acetoxy-2,3,5-trimethylphenoxy)-3-isopropylaminopropan-2-ol) (metipranolol);

(1-(isopropylamino)-3-(o-methoxyphenoxy)-3-[(1-methylethyl)amino]-2-propanol) (moprolol);

((1-tert.butylamino)-3-[(5,6,7,8-tetrahydro-cis 6,7-dihydroxy-1-naphthyl)oxy]-2-propanol) (nadolol)

((S)-1-(2-cyclopentylphenoxy)-3-[(1,1-dimethylethyl)amino]-2-propanol sulfate (2:1)) (penbutolol);

(4'-[1-hydroxy-2-(amino)ethyl]methanesulfonanilide) (sotalol);

(2-methyl-3-[4-(2-hydroxy-3-tert.butylaminopropoxy)-phenyl]-7-methoxy-isoquinolin-1-(2H)-one);

(1-(4-(2-(4-fluorophenyloxy)ethoxy)phenoxy)-3-isopropylamino-2-propanol HCl);

((−)-p-[3-[(3,4-dimethoxyphenethyl)amino]-2-hydroxypropoxy]-β-methylcinnamonitrile) (pacrinolol);

((±)-2-(3'-tert.butylamino-2'-hydroxypropylthio)-4-(5'-carbamoyl-2'-thienyl) thiazole HCl) (arotinolol);

((±) 1-[p-[2-(cyclopropylmethoxy)ethoxy]phenoxy]-3-(isopropylamino)-2-propanol) (cicloprolol);

((±)-1-[(3-chloro-2-methylindol-4-yl)oxy]-3-[(2-phenoxyethyl)amino]-2-propanol) (indopanolol);

((±) 6-[[2-[[3-(p-butoxyphenoxy)-2-hydroxypropyl]amino]ethyl]amino]-1,3 dimethyluracil) (pirepolcl);

(4-(cyclohexylamino)-1-(1-naphtholenyloxy)-2-butanol);

(1-phenyl-3-2-[3-(2-cyanophenoxy)-2-hydroxypropyl]-aminoethyl]hydantoin HCl);

(3,4-dihydro-8-(2-hydroxy-3-isopropylaminopropoxy)-3-nitroxy-2H-1-benzopyran) (nipradolol);

α- and β-Adrenergic Blocking Agents:

((±)-1-tert-butylamino)-3-[o-[2-(3-methyl 5-isoxazolyl)vinyl]phenoxy]-2-propanol) (isoxaprolol);

(1-isopropylamino-3-(4-(2-nitroxyethoxy)phenoxy)-2-propanol HCl);

(4-hydroxy-α-[[3-(4-methoxyphenyl)-1-methylpropyl]-aminomethyl]-3-(methylsulfinyl)-benzmethanol HCl) (sulfinalol);

(5-[1-hydroxy-2-[[2-(o-methoxyphenoxy)ethyl]amino]-ethyl]-2-methylbenzenesulfonamide HCl);

(5-[1-hydroxy-2-[(1-methyl-3-phenylpropyl)amino]ethyl]-salicylamide HCl) (labetalol);

(1-((3-chloro-2-methyl-1H-indol-4-yl)oxy)-3-((2-phenoxyethyl)amino)-2-propanol -hydrogenmalonate) (ifendolol);

(4-(2-hydroxy-3-[(1-methyl-3-phenylpropyl)amino]-propoxy)benzeneacetamide);

(1-[3-[[3-(1-naphthoxy)-2-hydroxypropyl]-amino]-3,3-dimethyl-propyl]-2-benzimidazolinone);

(3-(1-(2-hydroxy-2-(4-chlorophenylethyl)-4-piperidyl]-3,4-dihydroxy)quinoxolin-2-(1H) -one);

CNS-Acting Agents: clonidine; methyldopa;

Adrenergic Neuron Blocking Agents: quanethidine; reserpine and other rauwolfia alkaloids such as rescinnamine;

Vasodilators: diazoxide; hydralazine; minoxidil;

Angiotensin I Converting Enzyme Inhibitors:

1-(3-mercapto-2-methyl-1-oxopropyl)-L-proline (captopril);

(1-(4-ethoxycarbonyl-2,4-(R,R)-dimethylbutanoyl)-indoline-2(S)-carboxylic acid);

(2-[2-[[1-(ethoxycarbonyl)-3-phenyl propyl]amino]-1-oxopropyl]-1,2,3,4-tetrahydro-3-isoquinoline carboxylic acid);

((S)-1-[2-[[1-(ethoxycarbonyl)-3-phenylpropyl]amino]-1-oxopropyl]octahydro-1H-indole-2-carboxylic acid HCl);

(N cyclopentyl-N-(3-(2,2-dimethyl-1-oxopropyl)thiol-2-methyl-1-oxopropyl)glycine) (pivalopril);

((2R,4R)-2-(2-hydroxyphenyl)-3-(3-mercaptopropionyl)-4-thiazolidinecarboxylic acid);

(1-(N[1-(S)-ethoxycarbonyl-3-phenylpropyl]-(S)-alanyl)-cis,syn-octahydroindol-2(S) carboxylic acid HCl);

((−)-(S)-1-[(S)-3-mercapto-2-methyl-1-oxopropyl]-indoline-2-carboxylic acid);

([1(S),4S]-1-[3-(benzoylthio)-2-methyl-1-oxopropyl]-4-phenylthio L-proline;

(3-([1-ethoxycarbonyl-3-phenyl-(1S)-propyl]amino)-2,3,4,5-tetrahydro-2-oxo-1-(3S) -benzazepine-1-acetic acid HCl);

(N-(2-benzyl-3-mercaptopropanoyl)-S-ethyl-L-cysteine) and the S methyl analogue;

(N-(1(S)-ethoxycarbonyl-3-phenylpropyl)-L-alanyl-L-proline maleate) (enalapril);

N-[1-(S)-carboxy-3-phenylpropyl]-L-alanyl-1-proline;

$N^2$-[1-(S)-carboxy-3-phenylpropyl]-L-lysyl-L-proline (lysinopril);

Calcium Channel Blockers: α3-[[2-(3,4-dimethoxyphenyl)ethyl]methylamino]propyl]-3,4-dimethoxy-α-(1-methylethyl) benzeneacetonitrile (verapamil);

1,4-dihydro-2,6-dimethyl-4-(2-nitrophenyl)-3,5-pyridinedicarboxylic acid dimethyl ester (nifedipine);

2-(2,2-dicyclohexylethyl)piperidine (perhexiline);

N-(1-methyl-2-phenylethyl)- -phenylbenzenepropanamine (prenylamine);

3-(aminosulfonyl)-4-chloro-N-(2,3-dihydro-2-methyl-1H-indol-1-yl)benzamide (indapamide);

(2'-(2-diethylaminoethoxy)-3-phenylpropiophenone (etafenone);

(4-[4,4-bis-(4-fluorophenyl)butyl]-N-(2,6-dimethylphenyl)-1-piperazineacetamide) (lidoflazine);

(2-(N-benzyl-N-methylamino)ethylmethyl-2,6 dimethyl-4-(m-nitrophenyl)-1,4-dihydro-3,5-pyridinedicarboxylate HCl) (nicardipine);

(N-(3,4-dimethoxyphenethyl)-2-(3,4-dimethoxyphenyl)-N-methyl-m-dithiane-2-propylamine-1,1,3,3-tetraoxide) (tiapamil);

(5,6-dimethoxy-2-(3-[(α-(3,4-dimethoxy)phenylethyl)-methylamino]propyl)phthalimidine) (falipamil);

(β-[(2-methylpropoxy)methyl]-N-phenyl-N-phenylmethyl-1-pyrrolidineethanamine HCl monohydrate) (bepridil);

((+)-cis-3-(acetyloxy)-5-[2-(dimethylamino)ethyl]-2,3-dihydro-2-(4-methoxyphenyl)-1,5-benzothiazepin-4-(5H)-one) (diltiazem);

((E)-1-[bis-(p fluorophenyl)methyl]-4-cinnamylpiperazine di HCl) (flunarizine);

(5-[(3,4-dimethoxyphenethyl)methylamino]-2-isopropyl-2-(3,4,5-trimethoxyphenyl)valeronitrile (gallopamil);

(ethylmethyl(2,3-dichlorophenyl)-1,4-dihydro-2,6-dimethyl-3,5-pyridinedicarboxylate (felodipine);

(isopropyl-2-methoxyethyl-1,4-dihydro-2,6-dimethyl-4-(3-nitrophenyl)-3,5-pyridinecarboxylate) (nimodipine);

(3-ethyl-5-methyl-1,4-dihydro-2,6-dimethyl-4-(3-nitrophenyl)-3,5-pyridine-dicarboxylate) (nitrendipine);

Other Antihypertensive Agents: aminophylline; cryptenamine acetates and tannates; deserpidine; meremethoxylline procaine; pargyline; trimethaphan camsylate; and the like, as well as admixtures and combinations thereof.

Typically, the individual daily dosages for these combinations can range from about one-fifth of the minimally-recommended clinical dosages to the maximum recommended levels for the entities when they are given alone. Coadministration is most readily accomplished by combining the active ingredients into a suitable unit dosage form containing the proper dosages of each. Other methods of coadministration are, of course, possible.

The renin inhibitory novel peptides of the present invention may also be utilized in in vivo or in vitro diagnostic methods for the purpose of establishing the significance of renin as a causative or contributory factor in hypertension, hyperaldo steronism or congestive heart failure in a particular patient.

In the in vivo method, a novel peptide of the present invention is administered to a patient, preferably by intravenous injection, although parenteral administration is also suitable, at a hypotensive dosage level in a single dose of from 0.1 to 10 mg per kg of body weight, and the resulting transitory fall in blood pressure, if it occurs, indicates supranormal plasma renin levels.

In vitro methods which may be employed involve incubating a body fluid, preferably plasma, with a novel peptide of the present invention according to methods described in Boger et al., *J. Med. Chem.*, 1985, 28, 1779–1790.

The following are intended to exemplify the present invention, without, however, limiting it.

EXAMPLE 1

SYNTHESIS OF STARTING LACTAMS

A. Preparation of 1-Methylcaprolactam

Caprolactam (25 g; 0.22 mol) was added portionwise over a period of 15 minutes to a suspension of NaH (10.6 g of a 60% suspension in mineral oil; 0.265 mol) in degassed DMF (500 mL). The mixture was stirred for 3 hours at room temperature under an atmosphere of nitrogen and was then cooled to 0° C. Methyl iodide (39.5 g; 0.275 mol) was added dropwise to the cold suspension over a period of 30 minutes, and stirring was continued overnight, allowing the cooling bath to warm to room temperature.

Acetic acid (ca. 2 mL) was added to quench any remaining NaH, and the suspension was filtered, with the bulk of the DMF being removed by distillation at reducted pressure (ca. 20 torr), until NaI had formed a heavy precipitate. Ether was added and the mixture was cooled for several hours in a refrigerator.

The NaI was removed by filtration, and after the ether had been removed under reduced pressure on the rotovap, distillation under reduced pressure was re-. sumed. 1 Methylcaprolactam (20 g; 71% yield) was collected, boiling at 110–115° C. (10 torr).

B. Preparation of 4-Methyl-3 Morpholinone

The title compound was prepared from 2 (methylamino)ethanol nd chloroacetyl chloride in basic ethanol using the procedure of Surry, et. al., *J. Am. Chem. Soc.* (1955) 77, 633. The product was purified by vacuum distillation from calcium hydride, bp 108–112° C. (10 torr).

C. Preparation of 1-Butyl 2-Piperidinone

2-Piperidinone is deprotonated with NaH in DMF solution and butylated with n-butyl iodide to give the title compound.

D. Preparation of 1-Butyl-6,6-Dimethyl-2-Piperidinone

The oxime of 2,2 dimethylcyclopentanone is prepared by reaction of the ketone with hydroxylamine hydrochloride in EtOH, and treated with p-toluenesulfonyl chloride and DMAP. Heating then effects Beckmann rearrangement to give 6,6-dimethyl-2-piperidinone which is deprotonated with NaH in DMF solution. Reaction with n-butyl iodide then gives the title compound.

E. Preparation of 1-(2-Diethylaminoethyl)-2-Piperidinon

2-Piperidinone is deprotonated with NaH in DMF solution and reaction with allyl bromide, and 1-allyl-2-piperidinone is obtained by distillation. Ozonolysis in MeOH solution at −78° C., followed by reductive workup with Me$_2$S, gives the aldehyde derivative, which is reductively aminated using diethylamine hydrochloride and NaBH$_4$ to give the title compound.

F. Preparation of 1.5.5 Trimethyl-2-Piperidinone

The oxime of 3,3 dimethylcyclopentanone is prepared by treatment of the ketone with hydroxylamine hydrochloride in EtOH. Heating the oxime with p-toluenesulfonyl chloride and DMAP effects Beckmann rearrangement to give a mixture of 4,4-dimethyl 2-piperidinone and the desired 5,5-dimethyl-2-piperidinone.

This mixture is separated chromatographically and the 5,5-dimethyl-2-piperidinone is methylated by reaction with NaH in DMF solution followed by treatment with methyl iodide to give the title compound.

G. Preparation of 4 Methyl-5-(2-Propyl)-3-Morpholinone

Treatment of valinol in basic ethanol with chloroacetyl chloride using the procedure of Surry, et. al., *J. Am. Chem. Soc.* (1955) 77, 633, gives 5-(2-propyl)-3-morpholinone. Deprotonation of the latter with NaH in DMF solution and reaction with methyl iodide gives the title compound.

H. Preparation of 4-Methyl-3-Thiamorpholinone

Heating N methylaziridine with ethyl mercaptoacetate gives the title compound.

EXAMPLE 2

SYNTHESIS OF BOC-(ACHP)-LACTAMS

A. Preparation of Boc-(ACHP)-1-Methyl-2-Piperidinone using a Typical Lactam Aldol Addition Procedure To a 0° C. solution of diisopropylamine (4.11 g; 40.7 mmol) in dry THF (120 mL) under an atmosphere of nitrogen was added n-butyllithium (25.1 mL of a 1.6 M solution in hexane: 40.1 mmol). After being stirred for 10 minutes, the resulting solution was cooled to −78° C., at which time a solution of 1-methyl2-piperidinone (4.52 g, 40.0 mmol) in dry THF (10 mL) was added dropwise over a period of 5 minutes.

The resulting solution was stirred at −78° C. for 1.5 hour, when a 78° C. solution of N-Boc-L-cyclohexylalaninal (10.2 g; 40.0 mmol), prepared according to the method of Boger, et. al., *J. Med. Chem.*, (1985) 28, 1779, in dry THF (60 mL) was added rapidly via cannula. After being stirred for 5 minutes at −78° C., the reaction was quenched by the addition of 10 mL of water, and the cooling bath was removed and more water (25 mL) and ether (200 mL) were added.

The mixture was extracted with 5% aqueous HCl (200 mL), saturated with aqueous NaHCO$_3$ (200 mL), and dried (MgSO$_4$) and filtered. Removal of the solvents under reduced pressure gave a viscous oil, from which the diasteriomeric aldol products was separated by flash chromatography (SiO$_2$; 2%–5% MeOH/CH$_2$Cl$_2$).

The 2S,3S,4S diasteriomer was obtained as a viscous oil (2.80 g; 19% yield).

B. Preparation of Boc (ACHP)-4-Methyl-3-Morpholinone

The title compound (2S,3S,4S diasteriomer) was obtained by aldol reaction of Boc-L-cyclohexylalaninal and 4 methyl 3 morpholinone using the procedure described in Example 2A.

C. Preparation of Boc-(ACHP)-1-Methylcaprolactam

The title compound (2S,3S,4S, diasteriomer) was obtained by aldol reaction of Boc-L cyclohexylalaninal and 1-methylcaprolactam using the procedure described in Example 2A.

The following Boc—(ACHP)—lactams are prepared using the aldol procedure described in Example 2A D. Boc-(ACHP 1-Butyl-2-Piperidinone E. Boc-(ACHP)-1-(2-Diethylaminoethyl)-2-Piperidinone F. Boc-(ACHP) 1-Butyl-6,6-Dimethyl-2-Piperidinone G. Boc-(ACHP)-1,5,5 Trimethyl-2-piperidinone H. Boc-(ACHP)-4-Methyl-3-thiamorpholinone I. Boc-(ACHP)-4-Methyl-5-(2-Propyl)-3-Morpholinone

EXAMPLE 3

AMINO ACID COUPLING PROCEDURES AND SUBSEQUENT TRANSFORMATIONS

A. Preparation of Boc-Phe-His-(ACHP)-1-Methyl-2-Piperidinone

Step 1.
Boc-(DNP)His-(ACHP)-1-Methyl-2-Piperidinone

To a solution of Boc (ACHP) 1 methyl 2-piperidinone (2.20 g; 5.98 mmol) in CH$_2$Cl$_2$ (4 mL) was added TFA (4 mL) and the solution was stored under an atmosphere of nitrogen at ambient temperature for 45 minutes. Excess TFA and solvent were removed under reduced pressure and the oil so obtained was triturated in ether, giving a white solid which was collected by filtration, washed with ether, and dried under reduced pressure.

The TFA salt (2.10 g; 92% yield) was dissolved under an atmosphere of nitrogen in a minimum amount (5–6 mL) of DMF (more ideally in EtOAc if the salt had been soluble) and stored while the activation of Boc(DNP)His—OH was accomplished by in situ formation of a mixed anhydride, as described immediately below.

(Activation of Boc(DNP)His—OH) To a suspension of Boc(DNP)His OH (3.23 g; 7.69 mmol) in dry EtOAc (30 mL) under an atmosphere of nitrogen was added NMM (930 ul; 8.45 mmol), which caused dissolution of any remaining solid. The solution was cooled to −23° C. at which point isobutyl chloroformte (957 ul; 7.38 mmol) was added, and the resulting solution was stirred at −23° C. for 25 minutes.

After completion of the activation, the DMF solution of the TFA salt was neutralized by the addition of NMM (812 ul; 7.38 mmol) and was added via cannula to the cold solution of the mixed anhydride. After being stirred for 1 hour at −23° C., the reaction mixture was warmed to 0° C. and was stirred for 1.5 hour. The cooling bath was removed and stirring of the mixture was continued for another 3 hours, at which time the reaction was quenched by the addition of water (50 mL).

The mixture was diluted with EtOAc (125 mL) and was washed successively with 5% aqueous HCl (150 mL), water (20 mL), and saturated aqueous NaHCO$_3$ (200 mL). The organic layer was dried (MgSO$_4$), filtered, and concentrated under reduced pressure to give an orange solid which was flash chromatographed (SiO$_2$; 3%–5% MeOH/CH$_2$Cl$_2$).

The coupling product was obtained as a yellow solid (3.05 g; 75% yield).

Step 2 Boc-Phe-(DNP)His (ACHP)-1-Methyl-2-Piperidinone

To a solution of the coupling product obtained from Step 1 (3.05 g; 4.55 mmol) in CH$_2$Cl$_2$ (4 mL) was added TFA (4 mL), and the mixture was stored under an atmosphere of nitrogen for 45 minutes, at which time the solvent and excess TFA were removed under reduced pressure. The yellow oil so obtained was triturated in ether and the solid which resulted was collected by filtration, washed with ether, and dried under reduced pressure.

The resulting orange yellow solid (2.99 g; 96% yield) was dissolved, under an atmosphere of nitrogen, in dry EtOAc (20 mL) and stored while the activation of Boc-Phe-Oh was accomplished by in situ formation of a mixed anhydride as described below.

(Activation of Boc—Phe—OH) To a suspension of Boc—Phe—OH (1.52 g; 5.74 mmol) in dry EtOAc (25 mL) under an atmosphere of nitrogen was added NMM (695 μl; 6.31 mmol). The resulting solution was cooled to −23° C., isobutyl chloroformate (715 ul; 5.51 mmol) was added, and the solution was stirred for 25 minutes.

After completion of the activation, the solution of the TFA salt was neutralized by the addition of NMM (555 μl; 5.06 mmol) and was added via cannula to the cold solution of the mixed anhydride. The resulting mixture was stirred at −23° C. for 1 hour, at 0° C. for 1.5 hour, and then at room temperature for 3.5 hours, and the reaction was quenched by the addition of water (50 mL), and was diluted with EtOAc (125 mL).

The organic phase was washed successively with 5% aqueous HCl (150 mL), water (20 mL) and saturated aqueous NaHCO$_3$ (150 mL), then dried (MgSO$_4$), and filtered. Removal of the solvent under reduced pressure gave a solid which was flash-chromatographed (SiO$_2$; 4%–7% MeOH/CH$_2$Cl$_2$). The coupling product was obtained as a yellow solid (3.24 g; 87% yield).

Step 3. Boc-Phe-His-(ACHP)-1-Methyl-2-Piperidinone

The coupling product obtained from Step 2 (3.24 g; 3.96 mmol) was dissolved under an atmosphere of nitrogen in dry CH$_2$Cl$_2$ (8 mL), then thiophenol (4 mL) and NMM (60 μl; 0.54 mmol) were added. The mixture was stirred at room temperature for 5 hours, at which time the solvent and excess thiophenol were removed under reduced pressure (0.2 torr) at 30° C. The residue was flash chromatoqraphed (SiO$_2$; 5%–10%

MeOH/CH₂Cl₂), giving the title compound as an off-white powder (2.27 g; 88% yield).

The product exhibited satisfactory NMR spectral properties, was analzyed for purity by reverse phase HPLC, and was anlyzed for composition using C, H, and N combustion analysis. Inhibition of human plasma renin was assayed using the in vitro method described by Boger, et. al., *J. Med. Chem.* (1985) 28, 1779. IC$_{50}$=47 nM.

B. Preparation of Boc-Phe His-(ACHP)-4-Methyl-3-Morpholinone

Amino acid coupling was accomplished as described in Example 3A. IC$_{50}$=31 nM.

C. Preparation of Boc Phe His-(ACHP) 1-Methylcaprolactam

Amino acid coupling was accomplished as described in Example 3A. IC$_{50}$=203 nM.

D. Preparation of Boc-Phe-His-(ACHP)-1-(N-Benzyl-2-Diethylaminoethyl)-2-Piperidinone Acetate Boc-Phe-His-(ACHP)-1-(Diethylaminoethyl)-2-piperidinone is protected on the histidine side chain by reaction with (BOC)₂O in DMF solution. An excess of benzyl bromide is added and the mixture is warmed to effect quaternization of the diethylaminoethyl substituent. The Boc group on the histidine side chain is removed in situ by the addition of water and triethylamine.

The crude product is purified by preparative reverse phase HPLC and is passed through an ion exchange column (Bio Rad AG3-X4A resin, acetate form) to produce the title compound. Ipoc—Phe—His—peptides are made using sequential coupling, using Ipoc—Phe instead of Boc—Phe, in the method according to Example 3A, or by fragment coupling, using Ipoc—Phe—His in place of Boc—Phe—His, in the method according to Example 3B.

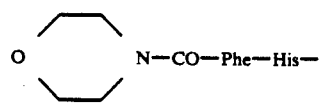

peptides are made by sequential coupling using mixed anhydride coupling (according to Example 3A) for the histidine group, and using mixed anhydride or DCC/HOBT coupling for the

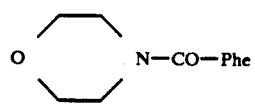

group. (CH₃)₂CH—SO₂—Phe—His—peptides are made by sequential coupling using mixed anhydride coupling (according to Example 3A) for the histidine group, and using mixed anhydride or DCC/HOBT coupling for the (CH₃)₂CH-SO₂-Phe group.

(CH₃)₂CH—SO₂—CH₂—CH(CH₂Ph)—CO—His—peptides are made by sequential coupling using mixed anhydride coupling (according to Example 3A) for the histidine group and DCC/HOBT or DCC/HOSU coupling for the (CH₃)₂CH—SO₂—CH₂-CH(CH₂Ph)—CO—group.

2-Indolyl-CO His peptides are made by sequential coupling using mixed anhydride coupling (according to Example 3A) for the histidine group, and DCC or EDC coupling of indole-2-carboxylic acid.

These methods are applied to any of the 9 Boc-(ACHP)-lactams described in Example 2.

Claims to the Invention follow.

What is claimed is:

1. A peptide of the formula:

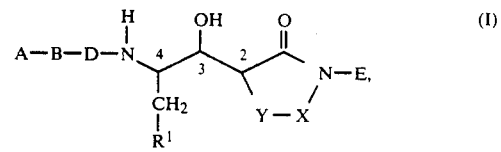

wherein:

A is hydrogen; C₁-C₆-alkyl; aryl, where aryl is unsubstituted or mono-, di- or trisubstituted phenyl, wherein the substituent(s) is/are independently selected from the group consisting of C₁-C₇alkyl, amino, mono- or di-C₁-C₄-alkylamino, amino-C₁-C₄-alkyl, hydroxy-C₁-C₄-alkyl, phenyl-C₁-C₄-alkyl, mono- or di-C₁-C₄-alkylamino-C₁-C₄-alkyl, guanidyl, guanidyl-C₁-C₄-alkyl, hydroxyl, C₁-C₄-alkoxy, trifluoromethyl, halo, CHO, —CO₂H, —CONH₂, —CONH-C₁-C₄-alkyl, —CON(C₁-C₄-alkyl)₂, —CO—C₁-C₄-alkyl, —(CH₂)$_m$—⊕N(R³)₂R⁴A⊖, where R³ is C₁-C₄-alkyl, —(CH₂)₄—, —(CH₂)₅- or —(CH₂)₂-O-(CH₂)₂-; R⁴ is C₁-C₄-alkyl, C₁-C₄-hydroxyalkyl, C₁-C₄-carboxyalkyl, or —CH₂-phenyl; A⊖is a counterion selected from the group consisting of single negatively charged ions; and m is 0-to-3; —CO₂—C₁-C₄-alkyl, —CO₂—C₁-C₄-alkoxy-C₂-C₄-alky

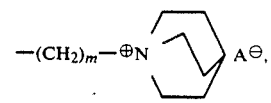

where A⁻and m are as defined above, and —NR⁵R⁶, where R⁵ and R⁶ are independently hydrogen, unsubstituted or monosubstituted C₁-C₄-alkyl, wherein the substituent is amino, mono- or di-C₁-C₄- alkylamino or —⊕N(R³)₂R⁴ A⊖, where R³, R⁴ and A⊖are as defined above; Het, where Het is an unsubstituted or mono-or disubstituted 5-or 6-membered mono- or bicyclic or benzofused 5-or 6-membered heterocyclic ring, where the one or two heteroatoms are independently selected from the group consisting of N, O, S, NO, SO, SO₂ or quaternized N, and the substituent(s) is/are independently selected from the group consisting of hydroxyl, thiol, C₁-C₆-alkyl, CF₃, C₁-C₄-alkoxy, halo, aryl, as defined above, aryl-C₁-C₄-alkyl, amino, mono- or diC-₁-C₄-alkylamino, amino-C₁-C₄-alkyl, hydroxy-C₁-C₄-alkyl, mono or di-C₁-C₄-alkylamino-C₁-C₄-alkyl, guanidyl, guanidylC₁-C₄-alkyl CHO, CO₂H, CO₂-C₁-C₄-alkyl, CONH₂, COHN-C₁-C₄-alkyl, CON(-C₁-C₄-alkyl)₂, NR⁵R⁶,

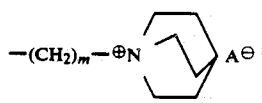

$A^{\oplus}$ and $-(CH_2)_m-\oplus N(R^3)_2(R^4 A^{\ominus}$, wherein $R^5$, $R^6$, $A^{\ominus}$, m, $R^3$ and $R^4$ are as defined above, or when the heteroatom is N, the substituents are alternatively $-(CH_2)_q-$ or $-(CH_2)_2-O-(CH_2)_2-13$ and form a ring with the N-atom, wherein q is 3-to-6;

where $R^2$ is $C_1-C_7$-alkyl; hydrogen; Het, as defined above; aryl, as defined above; mono-substituted $C_1-C_5$-alkyl, wherein the substituent is selected from the group consisting of aryl, as defined above; Het, as defined above; hydroxyl; $CO_2H$; $CO_2R^7$, where $R^7$ is $C_1-C_5$-alkyl, aryl, as defined above, and aryl-$C_1-C_4$-alkyl; $CONH_2$; $-CONH-R^7$ or $-S(O)_n-R^7$, wherein n is 0-to-2 and $R^7$ is as defined above; $C_1-C_4$-alkoxy; $C_3-C_7$-cycloalkyl; amino; mono- or di-$C_1-C_4$-alkylamino; NH-aryl, $-NH-CH_2$-aryl or $-CO$-aryl, where aryl is as defined above; and $-NH$-Het, $-NH-CH_2$-Het or $-CO$-Het, where Het is as defined above;

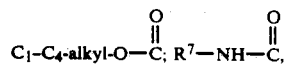

where $R^7$ is as defined above; or

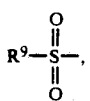

where $R^9$ is $C_1-C_5$-alkyl, aryl, as defined above, or Het, as defined above; B and D are independently

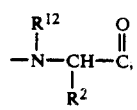

where $R^{12}$ is hydrogen, $C_1-C_5$-alkyl or $CH_2$-aryl, wherein aryl is as defined above; and $R^2$ is as defined above;

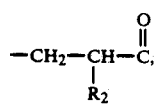

where $R^2$ is as defined above; or either B or D, but not both simultaneously, is absent;

$R^1$ is hydrogen; $C_3-C_6$-alkyl; aryl, as defined above; unsubstituted, mono-, di- or trisubstituted $C_3-C_7$-cycloalkyl, where the substituent(s) is/are selected from the group consisting of $C_1-C_4$-alkyl, trifluoromethyl, hydroxyl, $C_1-C_4$-alkoxy and halo; or unsubstituted or 4 monosubstituted 1,3-dithiolan-2-yl or unsubstituted or 4-mono-substituted 1,3-dithian-2-yl, where the substituent is $-(CH_2)_m$-aryl, where m and aryl are as defined above;

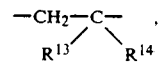

where $R^{13}$ and $R^{14}$ are independently hydrogen; $C_1-C_7$-alkyl; $C_2-C_7$-alkenyl; $-CO_2H$; $-CONH_2$; $-CO_2R^7$, $-CO-NH-R^7$ or $-CO-N(R^7)_2$, wherein $R^7$ is as defined above; mono-substituted $C_1-C_5$-alkyl, wherein the substituent is selected from the group consisting of azido; halo; hydroxy; $C_1-C_5$-alkoxy; aryl, aryl-$CH_2O$, aryloxy, aryl-$COO-$, aryl-$CH_2-NH-$ or arylamino, where aryl is as defined above; $C_1-C_5$-alkyl-$CO_2-$; $R^7NH-COO-$, $R^7-CO-NH-$, $R^7-NH-CO-NH-$ or $R^7-S(O)_n$, where n and $R^7$ are as defined above; amino; mono- or di-$C_1-C_4$-alkylamino; or Het, as defined above; or $R^{13}$ and $R^{14}$ are connected to form a polymethylene chain of the formula, $-(CH_2)_p$, where p is 2-to-6; or

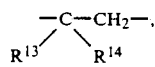

where $R^{13}$ and $R^{14}$ are as defined above;

Y is $CH_2$, O, S, SO or $SO_2$; or

Y—X is $-(CH_2)_4-$; and

E is hydrogen; aryl, as defined above; Het, as defined above; $C_2-C_7$-alkenyl; or unsubstituted or mono-substituted $C_1-C_7$-alkyl or unsubstituted or mono-substituted $C_3-C_7$-cycloalkyl, where the substituent is selected from the group consisting of aryl, $-CO$-aryl, $-NH$-aryl or $-O$-aryl, wherein aryl is as defined above; Het, $-NH$-Het, $-O$-Het, $-CO$-Het, $-NH-CO$-Het, $CO-NH$-Het, $CO-NH-CH_2$-Het or $O-CO$-Het, wherein Het is as defined above; azido; $C_3-C_7$-cycloalkyl; halo; hydroxyl; $C_1-C_4$-alkoxy; $-COOH$; $-O-CO-R^7$, $-O-CO-NH-R^7$, $-NH-CO-R^7$, $-NH-CO-NH-R^7$, $-S(O)_n-R^7$, $-CO_2R^7$ or $-CO-NH-R^7$, wherein $R^7$ and n are as defined above; amino; mono- or di-$C_1-C_4$-alkylamino; -CHO; and $-\oplus N(R^3)_2R^8A^{\ominus}$,

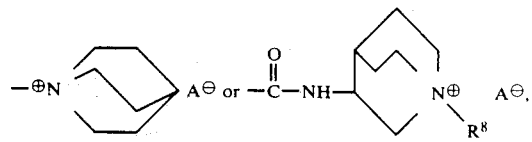

where $C_1-C_4$-alkyl, $C_1-C_4$-hydroxyalkyl, $C_1-C_4$-carboxyalkyl, $-CH_2$-aryl, wherein aryl is as defined above, or $-CH_2$-Het, wherein Het is as defined above, and $R^3$ and $A^{\ominus}$ are as defined above;

or a pharmaceutically-acceptable salt thereof.

2. A peptide according to claim 1, wherein A is $R^2-CO-$, $R^9-SO_2-$, $C_1-C_4$-alkyl-O-CO- or $R^7-NH-CO-$, wherein $R^2$, $R^7$ and $R^9$ are as defined in claim 1; B is absent when D is L-histidyl or L-valinyl, or B is unsubstituted or monosubstituted L-phenylalanyl, wherein the substituent is on the phenyl ring and is para-methoxy or

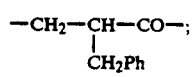

D is absent, when B is unsubstituted or monosubstituted L-phenylalanyl, or D is L-histidyl or L-valinyl; $R^1$ is cyclohexyl; Y is O or $CH_2$; $R^{13}$ and $R^{14}$ in either definition of X are simultaneously or independently hydrogen or methyl; and E is $C_1$-$C_6$-alkyl, $-(CH_2-)_r-{}^\oplus N(R^3)_2R^8\ CH_3CO^\ominus_2$, wherein r is 2 or 3 and $R^3$ and $R^8$ are as defined in claim 1,

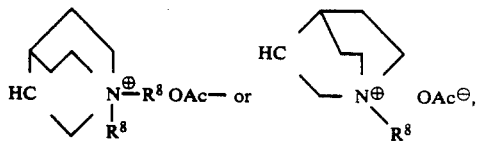

wherein $R^8$ is as defined in claim 1.

3. A peptide according to claim 1, having the structure:

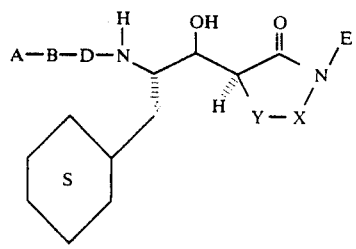

wherein in the structures:

| | A | B | D | Y | X | E |
|---|---|---|---|---|---|---|
| 1 | Boc<br>$(CH_3)_2CHSO_2-$ | Phe<br>" | His<br>" | $-CH_2-$<br>" | $-CH_2CH_2-$<br>" | n-Bu<br>" |
| | ![morpholine]<br>O⌒N—CO— | " | " | " | " | " |
| | $(CH_3)_2CHSO_2-$ | $-CH_2CH(CH_2Ph)-CO-$ | " | " | " | " |
| 5 | — | indole-2-CO— | " | " | " | " |
| | Boc<br>$(CH_3)_2CHSO_2-$ | Phe<br>" | His<br>" | $-CH_2$<br>" | $-CH_2C(CH_3)_2-$<br>" | n-Bu<br>" |
| | O⌒N—CO— | " | " | " | " | " |
| | $(CH_3)_2CHSO_2-$ | $CH_2CH(CH_2Ph)-CO-$ | " | " | " | " |
| 10 | — | indole-2-CO— | " | " | " | " |
| | Boc | " | " | " | $-CH_2CH_2-$ | $-(CH_2)_2-N^\oplus(Et)_2CH_2Ph$<br>$OAc^\ominus$ |
| | $(CH_3)_2CH-SO_2-$ | " | " | " | " | " |
| | O⌒N—CO— | " | " | " | " | " |
| | $(CH_3)_2CH-SO_2-$ | $CH_2CH(CH_2Ph)-CO-$ | His | $-CH_2$ | $-CH_2CH_2-$ | $-(CH_2)_2-N^\oplus(Et)_2CH_2Ph$<br>$OAc^\ominus$ |

-continued

| | A | B | D | Y | X | E |
|---|---|---|---|---|---|---|
| 15 | — | indole-2-CO— (1H) | " | " | " | " |
| | Boc | Phe | " | —O— | " | " |
| | (CH₃)₂CHSO₂— | " | " | " | " | " |
| | morpholine-N—CO— | " | " | " | " | " |
| | (CH₃)₂CH—SO₂— | CH₂CH(CH₂Ph)—CO— | " | " | " | " |
| 20 | — | indole-2-CO— (1H) | " | " | " | " |
| | Boc | Phe | His | —CH₂— | —C(CH₃)₂CH₂— | —(CH₂)₂N⊕(Et)₂CH₂Ph OAc⊖ |
| | (CH₃)₂CHSO₂— | " | " | " | " | " |
| | morpholine-N—CO— | " | " | " | " | " |
| | (CH₃)₂CH—SO₂— | CH₂CH(CH₂Ph)—CO— | " | " | " | " |
| 25 | — | indole-2-CO— (1H) | " | " | " | " |
| | Boc | Phe | His | —CH₂— | —CH₂CH₂— | HC⟨piperidine⟩N⊕(Et)₂⊖OAc |
| | (CH₃)₂CHSO₂— | " | " | " | " | " |
| | morpholine-N—CO— | " | " | " | " | " |
| | (CH₃)₂CH—SO₂— | CH₂CH(CH₂Ph)—CO— | " | " | " | " |
| 30 | — | indole-2-CO— (1H) | " | " | " | " |

-continued

| A | B | D | Y | X | E |
|---|---|---|---|---|---|
| Boc | Phe | His | —CH₂— | —CH₂CH₂— | HC—N⊕(Ph) ⊖OAc (cyclic) |
| (CH₃)₂CHSO₂— | " | " | " | " | " |
| O(CH₂CH₂)₂N—CO— | " | " | " | " | " |
| (CH₃)₂CH—SO₂— | CH₂CH(CH₂Ph)—CO— | " | " | " | " |
| 35 — | indol-2-yl-CO— | " | " | " | " |

4. A pharmaceutical composition for renin-associated hypertension or congestive heart failure comprising a pharmaceutical carrier and a therapeutically-effective amount of a peptide according to claim 1.

5. A pharmaceutical composition according to claim 4, also comprising an adjuvant.

6. A pharmaceutical composition according to claim 4, also comprising one or more compounds selected from the group consisting of:

Diuretics: acetazolamide; amiloride; bendroflumethiazide; benzthiazide; bumetanide; chlorothiazide; chlorthalidone; cyclothiazide; ethacrynic acid; furosemide; hydrochlorothiazide; hydroflumethiazide; indacrinone (racemic mixture, or as either the (+) or (−) enantiomer alone, or a manipulated ratio, e.g., 9:1 of said enantiomers, respectively); metolazone; methyclothiazide; muzolimine; polythiazide; quinethazone; sodium ethacrynate; sodium nitroprusside; spironolactone; ticrynafen; triamterene; trichlormethiazide;

α-Adrenergic Blocking Agents: dibenamine; phentolamine; phenoxybenzamine; prazosin; tolazoline;

β-Adrenergic Blocking Agents: atenolol; metoprolol; nadolol; propranolol; timolol;
  ((±)-2-[3-(tert butylamino)-2-hydroxypropoxy]-2-furananilide) (ancarolol);
  (2-acetyl-7-(2-hydroxy-3-isopropylaminopropoxy)-benzofuran HCl) (befunolol);
  ((±)-1-(isopropylamino)-3-(p (2-cyclopropylmethoxyethyl)-phenoxy)-2-propranol HCl) (betaxolol);
  (1-[(3,4-dimethoxyphenethyl)amino]-3-(m-tolyloxy)-2-propanol HCl) (bevantolol);
  ((±)-1-(4-((2-isopropoxyethoxy)methyl)phenoxy)-3-isopropylamino-2-propanol)fumarate) (bisoprolol);
  (4-(2-hydroxy-3-[4-(phenoxymethyl)-piperidino]-propoxy)-indole);
  (carbazolyl-4-oxy-5,2-(2-methoxyphenoxy)-ethylamino-2-propanol);
  (1-((1,1-dimethylethyl)amino)-3-((2-methyl-1H-indol-4-yl)oxy)-2-propanol benzoate) (bopindolol);
  (1-(2-exobicyclo[2.2.1]-hept-2-ylphenoxy-)-3-[(1-methylethyl)-amino]-2-propanol HCl) (bornaprolol);
  o-[-hydroxy-3-[(2-indol-3-yl-1,1-dimethylethyl)-amino]propoxy]benzonitrile HCl) (bucindolol);
  (α-[(tert.butylamino)methyl]-7-ethyl-2-benzofuranmethanol) (bufuralol);
  (3-[3-acetyl-4-[3-(tert.butylamino)-2-hydroxypropyl]-phenyl]-1,1-diethylurea HCl) (celiprolol);
  ((±)-2-[2-[3-[(1,1-dimethylethyl)amino]-2-hydroxypropoxy]phenoxy]N-methylacetamide HCl) (cetamolol);
  (2-benzimidazolyl phenyl(2-isopropylaminopropanol));
  ((±) 3'-acetyl-4'-(2-hydroxy-3-isopropylaminopropoxy)-acetanilide HCl) (diacetolol);
  (methyl-4-[2-hydroxy-3-[(1-methylethyl)aminopropoxy]]-benzenepropanoate HCl) (esmolol);
  (erythro-DL-1-(7-methylindan-4-yloxy)-3-isopropylaminobutan-2-ol);
  (1-(tert.butylamino)-3-[O-(2-propynyloxy)phenoxy]-2-propanol (pargolol);
  (1-(tert.butylamino)-3-[o-(6-hydrazino-3-pyridazinyl)-phenoxy]-2-propanol diHCl) (prizidilol);
  ((−)-2-hydroxy-5-[(R)-1-hydroxy-2-[(R)-(1-methyl-3-phenylpropyl)amino]ethyl]benzamide);
  (4-hydroxy-9-[2-hydroxy-3-(isopropylamino)-propoxy]-7-methyl-5H-furo[3,2-g][1]-benzopyran-5-one) (iprocrolol);
  ((−)-5-(tert.butylamino)-2-hydroxypropoxy]-3,4-dihydro-1-(2H)-naphthalenone HCl) (levobunolol);
  (4-(2-hydroxy-3-isopropylamino-propoxy)-1,2-benzisothiazole HCl);
  (4-[3-(tert.butylamino)-2-hydroxypropoxy]-N-methylisocarbostyril HCl);

((±)-N-2-[4-(2-hydroxy-3-isopropyl aminopropoxy)-phenyl]ethyl-N'-isopropylurea) (pafenolol);

(3-[[(2-trifluoroacetamido)ethyl]amino]-1-phenoxypropan2-ol);

(N-(3-(o-chlorophenoxy)-2-hydroxypropyl)-N'-(4'-chloro2,3-dihydro-3-oxo-5-pyridazinyl) ethylenediamine);

((±)-N-[3-acetyl-4-[2-hydroxy-3-[(1-methylethyl)amino]propoxy]phenyl]butanamide) (acebutolol);

((±)-4'-[3-(tert butylamino)-2-hydroxypropoxy]-spiro-cyclohexane-1,2'-indan]-1'-one) (spirendolol);

(7-[3-[[-2-hydroxy-3-[(2-methylindol-4-yl)oxy]-propyl]-amino]butyl]thiophylline) (teoprolol);

((±)-1-tert.butylamino-3-(thiochroman-8-yloxy)-2-propanol) (tertatolol);

((±) 1-tert.butylamino-3-(2,3-xylyloxy)-2-propanol HCl) (xibenolol);

(8-[3-(tert.butylamino)-2-hydroxypropoxy]-5-methylcoumarin) (bucumolol);

(2-(3-(tert.butylamino)-2-hydroxy-propoxy)benzonitrile HCl) (bunitrolol);

((±)-2'-[3-(tert-butylamino)-2-hydroxypropoxy-5'-fluorobutyrophenone) (butofilolol);

(1-(carbazol-4-yloxy)-3-(isopropylamino)-2-propanol) (carazolol);

(5-(3-tert.butylamino-2-hydroxy)propoxy-3,4-dihydrocarbostyril HCl) (carteolol);

(1-(tert.butylamino)-3-(2,5-dichlorophenoxy)-2-propanol) (cloranolol);

(1-(inden-4-(or 7-)yloxy)-3-(isopropylamino)-2-propanol HCl) (indenolol);

(1-isopropylamino-3-[(2-methylindol-4-yl)oxy]-2-propanol) (mepindolol);

(1-(4-acetoxy-2,3,5-trimethylphenoxy)-3-isopropylaminopropan-2-ol) (metipranolol);

(1-(isopropylamino)-3-(o-methoxyphenoxy)-3-[(1-methylethyl)amino]-2-propanol) (moprolol);

((1-tert.butylamino)-3-[(5,6,7,8-tetrahydro-cis-6,7-dihydroxy-1-naphthyl)oxy]-2-propanol) (nadolol)

((S)-1-(2-cyclopentylphenoxy)-3-[(1,1-dimethylethyl)amino]-2-propanol sulfate (2:1)) (penbutolol);

(4'-[1-hydroxy-2-(amino)ethyl]methanesulfonanilide) (sotalol);

(2-methyl-3-[4-(2-hydroxy-3-tert.butylaminopropoxy)phenyl]-7-methoxy-isoquinolin-1-(2H)-one);

(1-(4-(2-(4-fluorophenyloxy)ethoxy)phenoxy)-3-isopropylamino-2-propanol HCl);

((−)-p-[3-[(3,4-dimethoxyphenethyl)amino]-2-hydroxypropoxy]-β-methylcinnamonitrile) (pacrinolol);

((±)-2-(3'-tert.butylamino-2'-hydroxypropylthio)-4-(5'-carbamoyl2'-thienyl)thiazole HCl) (arotinolol);

((±)-1-[p-[2-(cyclopropylmethoxy)ethoxy]-phenoxy]-3-(isopropylamino)-2-propanol) (cicloprolol);

((±)-1-[(3-chloro-2-methylindol-4-yl)oxy]-3-[(2-phenoxyethyl)amino]-2-propanol) (indopanolol);

((±)-6-[[2-[[3-(p-butoxyphenoxy)-2-hydroxypropyl]-amino]ethyl]amino]-1,3-dimethyluracil) (pirepolol);

(4-(cyclohexylamino)-1-(1-naphtholenyloxy)-2-butanol);

(1-phenyl-3-[2-[3-(2-cyanophenoxy)-2-hydroxypropyl]aminoethyl]hydantoin HCl);

(3,4-dihydro-8-(2-hydroxy-3-isopropylaminopropoxy)-3-nitroxy-2H-1-benzopyran) (nipradolol);

α- and β-Adrenergic Blocking Agents:

((±)-1-tert-butylamino)-3-[o-[2-(3-methyl-5-isoxazolyl)vinyl]phenoxy]-2-propanol) (isoxaprolol);

(1-isopropylamino-3-(4-(2-nitroxyethoxy)phenoxy)-2-propanol HCl);

(4-hydroxy-α-[[3-(4-methoxyphenyl)-1-methylpropyl]aminomethyl]-3-(methylsulfinyl)-benzmethanol (HCl) (sulfinalol);

(5-[1-hydroxy-2-[[2-(o-methoxyphenoxy)ethyl]amino]ethyl]-2-methylbenzenesulfonamide HCl);

(5-[1-hydroxy-2-[(1-methyl-3-phenylpropyl)amino]ethyl]salicylamide HCl) (labetalol);

(1-((3-chloro-2-methyl-1H-indol-4-yl)oxy)-3-((2-phenoxyethyl)amino)-2-propanol hydrogenmalonate) (ifendolol);

(4-(2-hydroxy-3-[(1-methyl-3-phenylpropyl)amino]-propoxy)benzeneacetamide);

(1-[3-[[3-(1-naphthoxy-)-2-hydroxypropyl]-amino]-3,3-dimethyl-propyl]-2-benzimidazol (3-(1-(2-hydroxy-2-(4-chlorophenylethyl)-4-piperidyl)-3,4-dihydroxy)quinoxolin-2(1H)-one);

CNS-Acting Agents: clonidine; methyldopa;

Adrenergic Neuron Blocking Agents: quanethidine; reserpine and other rauwolfia alkaloids such as rescinnamine;

Vasodilators: diazoxide; hydralazine; minoxidil;

Angiotensin I Converting Enzyme Inhibitors:

1-(3-mercapto-2-methyl-1-oxopropyl)-L-proline (captopril);

(1-(4-ethoxycarbonyl-2,4-(R,R)-dimethylbutanoyl)-indoline-2(S)-carboxylic acid);

(2-[2-[[1-(ethoxycarbonyl)-3-phenyl-propyl]amino]-1-oxopropyl]-1,2,3,4-tetrahydro-3-3-isoquinoline carboxylic acid);

((S)-1-[2-[[1-(ethoxycarbonyl))-3-phenylpropyl]amino]-1-oxopropyl]octahydro-1H-indole -2-carboxylic acid HCl);

(N-cyclopentyl-N-(3-(2,2-dimethyl-1-oxopropyl)-thiol-2-methyl-1-oxopropyl)glycine) (pivalopril);

((2R,4R)-2-(2-hydroxyphenyl)-3-(3-mercaptopropionyl)-4-thiazolidinecarboxylic acid);

(1-(N-[1(S)-ethoxycarbonyl-3-phenylpropyl]-(S)-alanyl)-cis,syn-octahydroindol-2(S)-carboxylic acid HCl);

((−) (S)-1-[(S)-3-mercapto-2-methyl-1-oxopropyl]indoline-2-carboxylic acid);

([1(S),4S]-1-[3-(benzoylthio)-2-methyl-1-oxopropyl]-4-phenylthio-L-proline;

(3-([1-ethoxycarbonyl-3-phenyl-(1S) propyl]amino)-2,3,4,5-tetrahydro-2-oxo-1-(3S) -benzazepine-1-acetic acid HCl);

(N-(2-benzyl-3-mercaptopropanoyl)-S-ethyl L-cysteine) and the S methyl analogue;

(N-(1(S)-ethoxycarbonyl-3-phenylpropyl)-L-alanyl-L-proline maleate) (enalapril);

N-[1-(S)-carboxy-3-phenylpropyl]-L-alanyl-1-proline;

$N^2$-[1-(S)-carboxy-3-phenylpropyl]-L-lysyl-L-proline (lysinopril);

Calcium Channel Blockers:

α[3-[[2-(3,4 dimethoxyphenyl)ethyl]methylamino]-propyl]-3,4-dimethoxy-α-(1-methylethyl) benzene-acetonitrile (verapamil);
1,4-dihydro-2,6-dimethyl-4-(2-nitrophenyl)-3,5-pyridinedicarboxylic acid dimethyl ester (nifedipine);
2-(2,2-dicyclohexylethyl)piperidine (perhexiline);
N-(1-methyl-2-phenylethyl)- -phenylbenzenepropanamine (prenylamine);
3-(aminosulfonyl)-4-chloro-N-(2,3-dihydro-2-methyl-1H-indol-1-yl)benzamide (indapamide);
(2'-(2-diethylaminoethoxy)-3-phenylpropiophenone (etafenone);
(4-[4,4-bis-(4-fluorophenyl)butyl]-N-(2,6-dimethylphenyl)-1-piperazineacetamide) (lidoflazine);
(2-(N-benzyl-N-methylamino)ethylmethyl-2,6-dimethyl-4-(m-nitrophenyl)-1,4-dihydro-3,5-pyridinedicarboxylate HCl) (nicardipine);
(N-(3,4-dimethoxyphenethyl)-2-(3,4-dimethoxyphenyl)-N-methyl-m-dithiane-2-propylamine-1,1,3,3-tetraoxide) (tiapamil);
(5,6-dimethoxy-2-(3-[(α(3,4-dimethoxy)phenylethyl)-methylamino]propyl)phthalimidine) (falipamil);
(β[(2-methylpropoxy)methyl]-N-phenyl-N-phenylmethyl-1-pyrrolidineethanamine HCl monohydrate) (bepridil);
((±)-cis-3-(acetyloxy)-5-[2-(dimethylamino)ethyl]-2,3-dihydro-2-(4-methoxyphenyl)-1,5-benzothiazepin-4-(5H)-one) (diltiazem); (5H)-one) (diltiazem);
((E)-1-[bis-(p-fluorophenyl)methyl]-4-cinnamyl-piperazine di HCl) (flunarizine);
(5-[(3,4-dimethoxyphenethyl)methylamino]-2-isopropyl2-(3,4,5-trimethoxyphenyl)valeronitrile (gallopamil);
(ethylmethyl(2,3-dichlorophenyl)-1,4-dihydro-2,6-dimethyl-3,5-pyridinedicarboxylate (felodipine);
(isopropyl-2-methoxyethyl-1,4-dihydro-2,6-dimethyl-4-(3-nitrophenyl)-3,5-pyridinecarboxylate) (nimodipine);
(3-ethyl-5-methyl-1,4-dihydro-2,6-dimethyl-4-(3-nitrophenyl)-3,5-pyridine-dicarboxylate) (nitrendipine); and Other Antihypertensive Agents: aminophylline; cryptenamine acetates and tannates; deserpidine; meremethoxylline procaine; pargyline; tirmethaphan camsylate; and the like, as well as admixtures and combinations thereof.

7. A method of treating renin-associated hypertension or congestive heart failure in mammals comprising administering a therapeutically-effective amount of a peptide according to claim 1.

8. A method according to claim 7, wherein mammals are human and the therapeutically-effective amount is from 0.02 to 10 grams per day.

9. A method of diagnosing renin as a contributory factor in hypertension or congestive heart failure comprising administering to a patient from 0.1 to 10 mg/kg of body weight of the patient a peptide according to claim 1 and monitoring the patient's blood pressure for a transitory fall that would indicate supranormal plasma renin levels.

* * * * *